(12) United States Patent
Kuo et al.

(10) Patent No.: US 7,348,348 B2
(45) Date of Patent: Mar. 25, 2008

(54) ARYL-LINK-ARYL SUBSTITUTED THIAZOLIDINE-DIONE AND OXAZOLIDINE-DIONE AS SODIUM CHANNEL BLOCKERS

(75) Inventors: Howard C. H. Kuo, Plainfield, NJ (US); Michelle B. Ayer, Fanwood, NJ (US); Prasun K. Chakravarty, Edison, NJ (US); Peter T. Meinke, Plainfield, NJ (US); William H. Parsons, Belle Mead, NJ (US); Sriram Tyagarajan, Edison, NJ (US)

(73) Assignee: Merck & Co. Inc., Rahway, NJ (US)

( * ) Notice: Subject to any disclaimer, the term of this patent is extended or adjusted under 35 U.S.C. 154(b) by 376 days.

(21) Appl. No.: 10/512,924

(22) PCT Filed: Apr. 25, 2003

(86) PCT No.: PCT/US03/12910

§ 371 (c)(1),
(2), (4) Date: Oct. 29, 2004

(87) PCT Pub. No.: WO2004/024061

PCT Pub. Date: Mar. 25, 2004

(65) Prior Publication Data
US 2005/0165072 A1    Jul. 28, 2005

Related U.S. Application Data

(60) Provisional application No. 60/376,816, filed on Apr. 30, 2002.

(51) Int. Cl.
*A61K 31/425* (2006.01)
*C07D 277/00* (2006.01)

(52) U.S. Cl. ..................................... 514/369; 548/183
(58) Field of Classification Search ................ 548/183; 514/369
See application file for complete search history.

(56) References Cited

U.S. PATENT DOCUMENTS 5,643,932 A * 7/1997 Chihiro et al. ............... 514/365
6,518,268 B1 * 2/2003 Chin et al. ................ 514/236.8
7,122,564 B2 * 10/2006 Bernardon et al. ......... 514/357
2001/0036955 A1    11/2001 Gerritsen et al.

FOREIGN PATENT DOCUMENTS

WO    WO 02/062337 A1    8/2002

OTHER PUBLICATIONS

Sugimoto et al., 1996, CAS: 125:86633*
Yoshioka et al., 1993, CAS: 119:225943.*
Kagechika et al., 2001, CAS: 134:131526.*

* cited by examiner

*Primary Examiner*—Rei-tsang Shiao
(74) *Attorney, Agent, or Firm*—S. A. Ayler; W. Krovatin

(57) ABSTRACT

Aryl-link-aryl thiazolidine-dione and aryl-link-aryl oxazolidine-dione compounds are sodium channel blockers; pharmaceutical compositions that include an effective amount of the aryl-link-aryl thiazolidine-dione and aryl-link-aryl oxazolidine-dione compounds and a pharmaceutically acceptable carrier, and a method of treatment of acute pain, chronic pain, visceral pain, inflammatory pain, or neuropathic pain, as well as initable bowel syndrome, Cnohns disease, epilepsy, partial and generalized tonic seizures, multiple sclerosis, bipolar depression, and tachy-arrhythmias by the administration of an effective amount of aryl-link-aryl thiazolidine-dione and aryl-link-aryl oxazolidine-dione compounds are described.

12 Claims, No Drawings

ARYL-LINK-ARYL SUBSTITUTED THIAZOLIDINE-DIONE AND OXAZOLIDINE-DIONE AS SODIUM CHANNEL BLOCKERS

RELATED APPLICATION DATA

This is a National filing under 35 USC 371 of PCT/US03/12910, filed Apr. 25, 2003, which claims priority from U.S. Ser. No. 60/376,816, filed Apr. 30, 2002.

BACKGROUND OF THE INVNON

1. Field of the Invention

The present invention is directed to aryl-link-aryl thiazolidine-dione and aryl-link-aryl oxazolidine-dione compounds. In particular, this invention is directed to aryl-link-aryl thiazohdine-ione, and aryl-link-aryl oxazolidine-dione compounds which are sodium channel blockers useful in the treatment of chronic and neuropathic pain and disorders of the CNS including, but not limited to treatment of the symptoms of epilepsy, manic depression and bipolar disease.

2. Related Background

Voltage-gated ion channels allow electrically excitable cells to generate and propagate action potentials and therefore are crucial for nerve and muscle function. Sodium channels play a special role by mediating the rapid depolarization, which constitutes the rising phase of the action potential and in turn activates voltage-gated calcium and potassium channels. Voltage-gated sodium channels represent a multigene family. Nine sodium channel subtypes have been cloned and functionally expressed to date [Clare, J. J., Tate, S. N., Nobbs, M. & Romanos, M. A. Voltage-gated sodium channels as therapeutic targets. *Drug Discovery Today* 5, 506-520 (2000)]. They are differentially expressed throughout muscle and nerve tissues and show distinct biophysical properties. All voltage-gated sodium channels are characterized by a high degree of selectivity for sodium over other ions and by their voltage-dependent gating [Catterall, W. A. Structure and function of voltage-gated sodium and calcium channels. *Current Opinion in Neurobiology* 1, 5-13 (1991)]. At negative or hyperpolarized membrane potentials, sodium channels are closed. Following membrane depolarization, sodium channels open rapidly and then inactivate. Channels only conduct currents in the open state and, once inactivated, have to return to the resting state, favored by membrane hyperpolarization, before they can reopen. Different sodium channel subtypes vary in the voltage range over which they activate and inactivate as well as in their activation and inactivation kinetics.

Sodium channels are the target of a diverse array of pharmacological agents, including neurotoxins, antiarrhythmics, anticonvulsants and local anesthetics [Clare, J. J., Tate, S. N., Nobbs, M. & Romanos, M. A. Voltage-gated sodium channels as therapeutic targets. *Drug Discovery Today* 5, 506-520 (2000)]. Several regions in the sodium channel secondary structure are involved in interactions with these blockers and most are highly conserved. Indeed, most sodium channel blockers known to date interact with similar potency with all channel subtypes. Nevertheless, it has been possible to produce sodium channel blockers with therapeutic selectivity and a sufficient therapeutic window for the treatment of epilepsy (e.g. lamotrigine, phenytoin and carbamazepine) and certain cardiac arrhythmias (e.g. lignocaine, tocainide and mexiletine).

It is well known that the voltage-gated $Na^+$ channels in nerves play a critical role in neuropathic pain. Injuries of the peripheral nervous system often result in neuropathic pain persisting long after the initial injury resolves. Examples of neuropathic pain include, but are not limited to postherpetic neuralgia, trigeminal neuralgia, diabetic neuropathy, chronic lower back pain, phantom limb pain, and pain resulting from cancer and chemotherapy, chronic pelvic pain, complex regional pain syndrome and related neuralgias. It has been shown in human patients as well as in animal models of neuropathic pain, that damage to primary afferent sensory neurons can lead to neuroma formation and spontaneous activity, as well as evoked activity in response to normally innocuous stimuli [Carter, G. T. and B. S. Galer, *Advances in the management of neuropathic pain.* Physical Medicine and Rehabilitation Clinics of North America., 2001. 12(2): p. 447-459.]. The ectopic activity of normally silent sensory neurons is thought to contribute to the generation and maintenance of neuropathic pain. It is generally assumed to be associated with an increase in sodium channel activity in the injured nerve [Baker, M. D. and J. N. Wood, *Involvement of Na channels in pain pathways.* TRENDS in Pharmacological Sciences, 2001. 22(1): p. 27-31.]. Indeed, in rat models of peripheral nerve injury, ectopic activity in the injured nerve corresponds to the behavioral signs of pain. In these models, intravenous application of the sodium channel blocker and local anesthetic lidocaine can suppress the ectopic activity and reverse the tactile allodynia at concentrations that do not affect general behavior and motor function [Mao, J. and L. L. Chen, *Systemic lidocaine for neuropathic pain relief Pain,* 2000. 87: p. 7-17.]. Effective concentrations were similar to concentrations shown to be clinically efficacious in humans [Tanelian, D. L. and W. G. Brose, *Neuropathic pain can be relieved by drugs that are use-dependent sodium channel blockers: lidocaine, carbamazepine and mexiletne.* Anesthesiology, 1991. 74(5): p. 949-951.]. In a placebo-controlled study, continuous infusion of lidocaine reduced pain scores in patients with peripheral nerve injury, and in a separate study, intravenous lidocaine reduced pain intensity associated with postherpetic neuralgia (PHN) [Mao, J. and L. L. Chen, *Systemic lidocaine for neuropathic pain relief.* Pain, 2000. 87: p. 7-17. Anger, T., et al., *Medicinal chemistry of neuronal voltage-gated sodium channel blockers.* Journal of Medicinal Chemistry, 2001. 44(2): p. 115-137.]. Indeed, Lidoderm®, lidocaine applied in the form of a dermal patch, is currently the only FDA approved treatment for PHN [Devers, A. and B. S. Galer, *Topical lidocaine patch relieves a variety of neuropathic pain conditions: an open-label study.* Clinical Journal of Pain, 2000. 16(3): p. 205-208.].

In addition to neuropathic pain, sodium channel blockers have clinical uses in the treatment of epilepsy and cardiac arrhythmias. Recent evidence from animal models suggest that sodium channel blockers may also be useful for neuroprotection under ischaemic conditions caused by stroke or neural trauma and in patients with MS [Clare, J. J. et. al. And Anger, T. et. al.].

International Patent Publication WO 00/57877 describes aryl substituted pyrazoles, imidazoles, oxazoles, thiazoles, and pyrroles and their uses as sodium channel blockers. International Patent Publication WO 99/32462 describes triazine compounds for the treatment for CNS disorders. International Patent Publication WO 01/02377 describes thiazolidinediones as telomerase inhibitors.

However, there remains a need for novel compounds and compositions that therapeutically block neuronal sodium channels with minimal side effects.

SUMMARY OF THE INVENTION

The present invention is directed to aryl-link-aryl thiazolidine-dione and aryl-link-aryl oxazolidine-dione compounds which are sodium channel blockers useful in the of chronic and neuropathic pain and disorders of the CNS including, but not limited to treatment of the symptoms of epilepsy, manic depression and bipolar disease. This invention also provides a pharmaceutical composition which includes an effective amount of the novel aryl-link-aryl thiazolidine-dione or aryl-link-aryl oxazolidine-dione compounds, and a pharmaceutically acceptable carrier.

This invention further provides a method of treatment of acute pain, chronic pain, visceral pain, inflammatory pain, or neuropathic pain and disorders of the CNS including, but not limited to treatment of the symptoms of epilepsy, manic depression and bipolar disease by the administration of an effective amount of the novel aryl-link-aryl thiazolidine-dione or aryl-link-aryl oxazolidine-dione compounds.

DETAILED DESCRIPTION OF THE INVENTION

The compounds of the present invention are represented by Formula IA) or (IB):

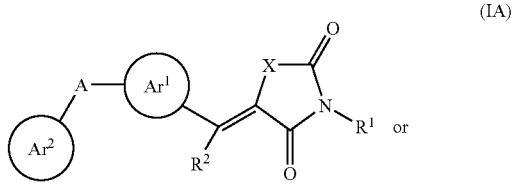

(IA)

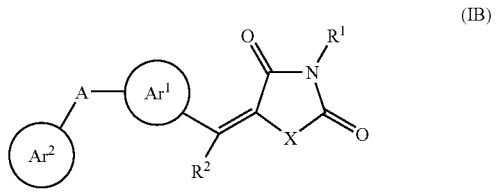

(IB)

or a pharmaceutically acceptable salt thereof, wherein

X is —S—, or —O—;

$R^1$ is hydrogen, —$C_{1-4}$alkyl, —$C_{1-4}$alkyl-N($C_{0-4}$alkyl)($C_{0-4}$alkyl), —$C_{0-4}$alkyl-CO—N($C_{0-4}$alkyl)($C_{0-4}$alkyl), —$C_{0-4}$alkyl-CO—O($C_{0-4}$alkyl), —$C_{1-4}$alkyl-piperidinyl, —$C_{1-4}$alkyl-morpholinyl, —$C_{1-4}$alkyl-pyrrolidinyl, —$C_{1-4}$alkyl-aryl, —$C_{1-4}$alkyl-aryl-aryl, optionally substituted with 1-6 independent halogen (F, Cl, Br or I), —CN, —$NO_2$, —$C_{1-4}$alkyl, —O—$C_{1-4}$alkyl, —N($C_{0-4}$alkyl)($C_{0-4}$alkyl), —$C_{0-4}$alkyl-CO—O($C_{0-4}$alkyl), —($C_{0-4}$alkyl)-NH—CO—O($C_{0-4}$alkyl), —($C_{0-4}$alkyl)-CO—N($C_{0-4}$alkyl)($C_{0-4}$alkyl), —S($C_{0-4}$alkyl), —S(O)($C_{1-4}$alkyl), —$SO_2$($C_{1-4}$alkyl), —$SO_2$N($C_{0-4}$alkyl)($C_{0-4}$alkyl), or —$NHSO_2$($C_{1-4}$alkyl) substituents;

$R^2$ is —$C_{0-4}$alkyl;

$Ar^1$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, and any of which is optionally substituted with 1-4 independent substituents selected from i) halogen, ii) —CN, iii) —$NO_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —$SO_2$($C_{1-4}$alkyl), xiii) —$SO_2$N($C_{0-4}$alkyl)($C_{0-4}$alkyl), xiv) —$NHSO_2$($C_{1-4}$alkyl), xv) —$C_{1-10}$ alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —$OSO_3$-$M^+$, —O—CO($C_{1-3}$alkyl)$CO_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$alkyl)-, —C(O)—, —CH(OH)—, —C=C—, —C≡C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —$OSO_3$-$M^+$, —O—CO($C_{1-3}$alkyl)$CO_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvii) —S(O)$_{1-2}$—($C_{1-6}$alkyl)-, xviii) —$C_{0-4}$alkyl-$C_{3-6}$cycloalkyl, or xix) —$C_{0-4}$alkyl-O—C(O)—$C_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

$Ar^2$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl , and any of which is optionally substituted with 1-5 independent substituents selected from i) halogen, ii) —CN, iii) —$NO_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —$SO_2$($C_{1-4}$alkyl), xiii) —$SO_2$N($C_{0-4}$alkyl)($C_{0-4}$alkyl), xiv) —$NHSO_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —$OSO_3$-$M^+$, —O—CO($C_{1-3}$alkyl)$CO_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$alkyl)-, —C(O)—, —CH(OH)—, —C=C—, —C≡C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —$OSO_3$-$M^+$, —O—CO($C_{1-3}$alkyl)$CO_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

A is —O—, S, CH$_2$, —N(C0-4alkyl)- or absent; and wherein aryl independently is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, and any of which is optionally substituted with 1-6 independent substituents selected from i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{0-4}$alkyl), xiii) —SO$_2$N(C$_{0-4}$alkyl)(C$_{0-4}$alkyl), xiv) —NHSO$_2$(C$_{0-4}$alkyl)(C$_{0-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl),—O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

M$^+$ is ammonium, sodium, lithium, potassium, calcium, magnesium, dicyclohexylamine, N-methyl-D-glucamine, arginine, or lysine; and any alkyl is optionally substituted with 1-6 independent halogen, phenyl, naphthyl, —N(C$_{0-4}$alkyl)(C$_{0-4}$alkyl), —C(O)—O(C$_{0-4}$alkyl), —CN, —NH—C(O)—O(C$_{0-4}$alkyl), —S(C$_{0-4}$alkyl), —NHSO$_2$(C$_{0-4}$alkyl)(C$_{0-4}$alkyl), or —SO$_2$N(C$_{0-4}$alkyl)(C$_{0-4}$alkyl) substituents.

The compounds of the present invention are also represented by Formula (IIA) or (IIB):

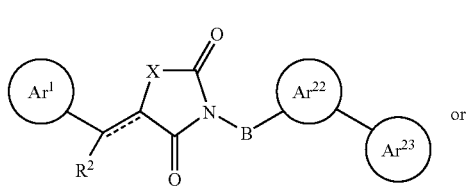

(IIA)

or

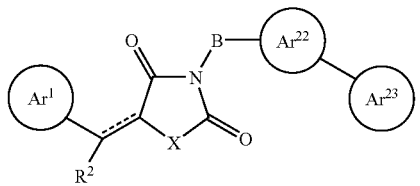

(IIB)

or a pharmaceutically acceptable salt thereof, wherein

X is —S—, or —O—;

R$^2$ is —C$_{0-4}$alkyl;

Ar$^1$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-,—C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

or optionally one of the substituents on Ar$^1$ is Ar$^2$, wherein Ar$^2$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$akyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)C$_{02}$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)i-$_2$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

B is —C$_{0-4}$alkyl-;

Ar$^{22}$ is phenyl optionally substituted with 1-4 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{1-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alky1)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

M$^+$ is ammonium, sodium, lithium, potassium, calcium, magnesium, dicyclohexylamine, N-methyl-D-glucamine, arginine, or lysine; and any alkyl is optionally substituted with 1-6 independent halogen, phenyl, naphthyl, —N(C$_{0-4}$alkyl)(C$_{0-4}$alkyl), —C(O)—O(C$_{0-4}$alkyl), —CN, —NH—C(O)—O(C$_{0-4}$alkyl), —S(C$_{0-4}$alkyl), —NHSO$_2$(C$_{0-4}$alkyl)(C$_{0-4}$alkyl), or —SO$_2$N(C$_{0-4}$alkyl)(C$_{0-4}$alkyl) substituents.

In one aspect, the compounds of the present invention are represented by Formula (IA) or (IB):

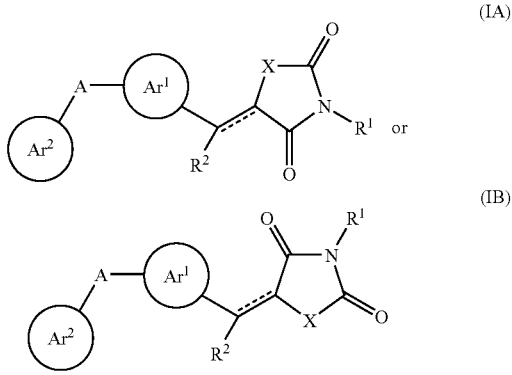

Ar$^{23}$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)- or a pharmaceutically acceptable salt thereof, wherein

X is —S—;

R$^1$ is hydrogen, —C$_{1-4}$alkyl, —C$_{1-4}$alkyl-N(C$_{0-4}$alkyl)(C$_{0-4}$alkyl), —C$_{0-4}$alkyl-CO—N(C$_{0-4}$alkyl)(C$_{0-4}$alkyl), —C$_{0-4}$alkyl-CO—O(C$_{0-4}$alkyl), —C$_{1-4}$alkyl-piperidinyl, —C$_{1-4}$alkyl-morpholinyl, —C$_{1-4}$alkyl-pyrrolidinyl, —C$_{1-4}$alkyl-aryl, —C$_{1-4}$alkyl-aryl-aryl, optionally substituted with 1-6 independent halogen, —CN, —NO$_2$, —C$_{1-4}$alkyl, —O—C$_{1-4}$alkyl, —N(C$_{0-4}$alkyl)(C$_{0-4}$alkyl), —C$_{0-4}$alkyl- CO—O($C_{0-4}$alkyl), —($C_{0-4}$alkyl)-NH—CO—O($C_{0-4}$alkyl), —($C_{0-4}$alkyl)-CO—N($C_{0-4}$alkyl)($C_{0-4}$alkyl), —S($C_{0-4}$alkyl), —S(O)($C_{1-4}$alkyl), —SO$_2$($C_{1-4}$alkyl), —SO$_2$N($C_{0-4}$alkyl)($C_{0-4}$alkyl), or —NHSO$_2$($C_{1-4}$alkyl) substituents;

$R^2$ is —$C_{0-4}$alkyl;

$Ar^1$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-4 independent i) halogen, ii) —CN, iii) —NO$_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —SO$_2$($C_{1-4}$alkyl), xiii) —SO$_2$N($C_{0-4}$alkyl)($C_{0-4}$alkyl), xiv) —NHSO$_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$alkyl)-, —C(O)—, —CH(OH)—, —C=C—, —C≡—C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvii) —S(O)$_{1-2}$—($C_{1-6}$alkyl)-, xviii) —$C_{0-4}$alkyl-$C_{3-6}$cycloalkyl, or xix) —$C_{0-4}$alkyl-O—C(O)—$C_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

$Ar^2$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —SO$_2$($C_{1-4}$alkyl), xiii) —SO$_2$N($C_{0-4}$alkyl)($C_{0-4}$alkyl), xiv) —NHSO$_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$alkyl)-, —C(O)—, —CH(OH)—, —C=C—, —C≡—C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvii) —S(O)$_{1-2}$—($C_{1-6}$alkyl)-, xviii) —$C_{0-4}$alkyl-$C_{3-6}$cycloalkyl, or xix) —$C_{0-4}$alkyl-O—C(O)—$C_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

A is —O—, —S—, —CH$_2$—, —N($C_{0-4}$alkyl)-, or absent;

wherein aryl independently is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-6 independent i) halogen, ii) —CN, iii) —NO$_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —SO$_2$($C_{1-4}$alkyl), xiii) —SO$_2$N($C_{0-4}$alkyl)($C_{0-4}$alkyl), xiv) —NHSO$_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$alkyl)-, —C(O)—, —CH(OH)—, —C=C—, —C≡—C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvii) —S(O)$_{1-2}$—($C_{1-6}$alkyl)-, xviii) —$C_{0-4}$alkyl-$C_{3-6}$cycloalkyl, or xix) —$C_{0-4}$alkyl-O—C(O)—$C_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

$M^+$ is ammonium, sodium, lithium, potassium, calcium, magnesium, dicyclohexylamine, N-methyl-D-glucamine, arginine, or lysine; and any alkyl is optionally substituted with 1-6 independent halogen, phenyl, naphthyl, —N($C_{0-4}$alkyl)($C_{0-4}$alkyl), —C(O)—O($C_{0-4}$alkyl), —CN, —NH—C(O)—O($C_{0-4}$alkyl), —S($C_{0-4}$alkyl), —NHSO$_2$($C_{0-4}$alkyl)($C_{0-4}$alkyl), or —SO$_2$N($C_{0-4}$alkyl)($C_{0-4}$alkyl) substituents.

In an embodiment of this one aspect, the compounds of the present invention are represented by Formula (IA) or (IB):

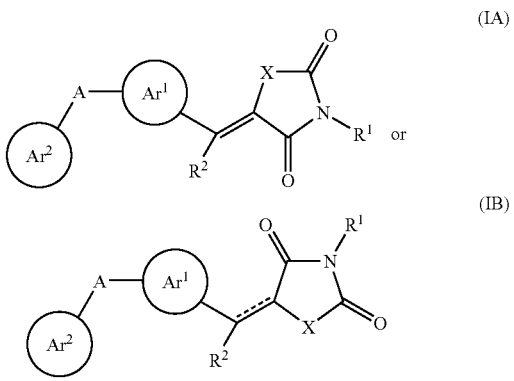

or a pharmaceutically acceptable salt thereof, wherein

X is —S—;

$R^1$ is hydrogen, —$C_{1-4}$alkyl, —$C_{1-4}$alkyl-N($C_{0-4}$alkyl)($C_{0-4}$alkyl), —$C_{0-4}$alkyl-CO—N($C_{0-4}$alkyl)($C_{0-4}$alkyl), —$C_{0-4}$alkyl-CO—O($C_{0-4}$alkyl), —$C_{1-4}$alkyl-piperidinyl, —$C_{1-4}$alkyl-morpholinyl, —$C_{1-4}$alkyl-pyrrolidinyl, —$C_{1-4}$alkyl-aryl, —$C_{1-4}$alkyl-aryl-aryl, optionally substituted with 1-6 independent halogen, —CN, —$NO_2$, —$C_{1-4}$alkyl, —O—$C_{1-4}$alkyl, —N($C_{0-4}$alkyl)($C_{0-4}$alkyl), —$C_{0-4}$alkyl-CO—O($C_{0-4}$alkyl), —($C_{0-4}$alkyl)-NH—CO—O($C_{0-4}$alkyl), —($C_{0-4}$alkyl)-CO—N($C_{0-4}$alkyl)($C_{0-4}$alkyl), —S($C_{0-4}$alkyl), —S(O)($C_{1-4}$alkyl), —$SO_2$($C_{1-4}$alkyl), —$SO_2$N($C_{0-4}$alkyl)($C_{0-4}$alkyl), or —$NHSO_2$($C_{1-4}$alkyl) substituents;

$R^2$ is —$C_{0-4}$alkyl;

$Ar^1$ is phenyl optionally substituted with 1-4 independent i) halogen, ii) —CN, iii) —$NO_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl),- ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —$SO_2$($C_{1-4}$alkyl), xiii) —$SO_2$N($C_{0-4}$alkyl)($C_{0-4}$alkyl), xiv) —$NHSO_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —$OSO_3$-$M^+$, —O—CO($C_{1-3}$alkyl)$CO_2$-$M^+$, —O—CO—($C_{1-6}$alkyl)-N($C_{0-6}$alkyl)($C_{0-6}$akyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$alkyl)-, —C(O)—, —CH(OH)—, —C=C—, —C≡C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —$OSO_3$-$M^+$, —O—CO($C_{1-3}$alkyl)$CO_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvii) —S(O)$_{1-2}$—($C_{1-6}$alkyl)-, xviii) —$C_{0-4}$alkyl-$C_{3-6}$cycloalkyl, or xix) —$C_{0-4}$alkyl-O—C(O)—$C_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

$Ar^2$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —$NO_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —$SO_2$($C_{1-4}$alkyl), xiii) —$SO_2$N($C_{0-4}$alkyl)($C_{0-4}$alkyl), xiv) —$NHSO_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —$OSO_3$-$M^+$, O—CO($C_{1-3}$alkyl)$CO_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$alkyl)-, —C(O)—, —CH(OH)—, —C=C—, —C≡C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —$OSO_3$-$M^+$, —O—CO($C_{1-3}$alkyl)$CO_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvii) —S(O)$_{1-2}$—($C_{1-6}$alkyl)-, xviii) —$C_{0-4}$alkyl-$C_{3-6}$cycloalkyl, or xix) —$C_{0-4}$alkyl-O—C(O)—$C_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

A is —O—, —S—, —$CH_2$—, —N($C_{0-4}$alkyl), or absent;

wherein aryl independently is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-6 independent i) halogen, ii) —CN, iii) —$NO_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —$SO_2$($C_{1-4}$alkyl), xiii) —$SO_2$N($C_{0-4}$alkyl)($C_{0-4}$alkyl), xiv) —$NHSO_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —$OSO_3$-$M^+$, —O—CO($C_{1-3}$alkyl)$CO_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alky)—C(O)—, —N($C_{0-6}$alkyl)-C(O)—N($C_{0-6}$alkyl)-, —C(O)—, —CH(OH)—, —C=C—, —C≡C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —$OSO_3$-$M^+$, —O—CO($C_{1-3}$alkyl)

—CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

M$^+$ is ammonium, sodium, lithium, potassium, calcium, magnesium, dicyclohexylamine, N-methyl-D-glucamine, arginine, or lysine; and any alkyl is optionally substituted with 1-6 independent halogen, phenyl, naphthyl, —N(C$_{0-4}$alkyl)(C$_{0-4}$alkyl), —C(O)—O(CO—alkyl), —CN, —NH—C(O)—O(C$_{0-4}$alkyl), —S(C$_{0-4}$alkyl), —NHSO$_2$(C$_{0-4}$alkyl)(C$_{0-4}$alkyl), or —SO$_2$N(C$_{0-4}$alkyl)(C$_{0-4}$alkyl) substituents.

In another embodiment of this one aspect, the compounds of the present invention are represented by Formula (IA) or (IB):

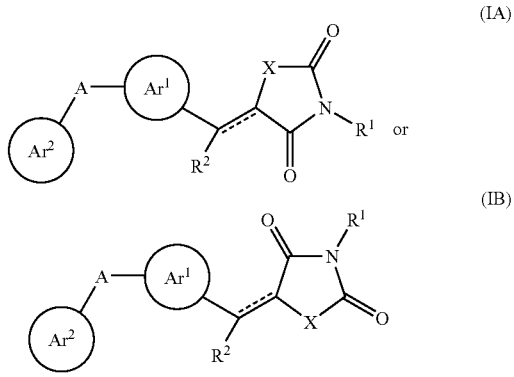

or a pharmaceutically acceptable salt thereof, wherein

X is —S—;

R$^1$ is hydrogen, —C$_{1-4}$alkyl, —C$_{1-4}$alkyl-N(C$_{0-4}$alkyl)(C$_{0-4}$alkyl), —C$_{0-4}$alkyl-CO—N(C$_{0-4}$alkyl)(C$_{0-4}$alkyl), —C$_{0-4}$alkyl-CO—O(C$_{0-4}$alkyl), —C$_{1-4}$alkyl-piperidinyl, —C$_{1-4}$alkyl-morpholinyl, —C$_{1-4}$alkyl-pyrrolidinyl, —C$_{1-4}$alkyl-aryl, —C$_{1-4}$alkyl-aryl-aryl, optionally substituted with 1-6 independent halogen, —CN, —NO$_2$, —C$_{1-4}$alkyl, —O—C$_{1-4}$alkyl, —N(C$_{0-4}$alkyl)(C$_{0-4}$alkyl), —C$_{0-4}$alkyl-CO—O(C$_{0-4}$alkyl), —(C$_{0-4}$alkyl)-NH—CO—O(C$_{0-4}$alkyl), —(C$_{0-4}$alkyl)-CO—N(C$_{0-4}$alkyl)(C$_{0-4}$alkyl), —S(C$_{0-4}$alkyl), —S(O)(C$_{1-4}$alkyl), —SO$_2$(C$_{1-4}$alkyl), —SO$_2$N(C$_{0-4}$alkyl)(C$_{0-4}$alkyl), or —NHSO$_2$(C$_{1-4}$alkyl) substituents;

R$^2$ is —C$_{0-4}$alkyl;

Ar$^1$ is thienyl optionally substituted with 1-2 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$aalkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O—M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C═C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

Ar$^2$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C═C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

A is —O—, —S—, —CH$_2$—, —N(C$_{0-4}$alkyl)-, or absent;

wherein aryl independently is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-6 independent i) halogen, ii) —CN, iii) —NO$_2$, iv) —CHO, v) —O—C$_{1-4}$alkyl, vi)

—N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

M$^+$ is ammonium, sodium, lithium, potassium, calcium, magnesium, dicyclohexylamine, N-methyl-D-glucamine, arginine, or lysine; and any alkyl is optionally substituted with 1-6 independent halogen, phenyl, naphthyl, —N(C$_{0-4}$alkyl)(C$_{0-4}$alkyl), —C(O)—O(C$_{0-4}$alkyl), —CN, —NH—C(O)—O(C$_{0-4}$alkyl), —S(C$_{0-4}$alkyl), —NHSO$_2$(C$_{0-4}$alkyl)(C$_{0-4}$alkyl), or —SO$_2$N(C$_{0-4}$alkyl)(C$_{0-4}$alkyl) substituents.

In still another embodiment of this one aspect, the compounds of the present invention are represented by Formula (IA) or (IB):

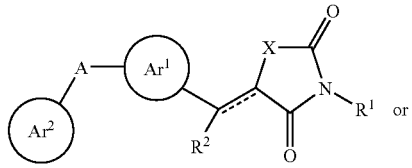
(IA)

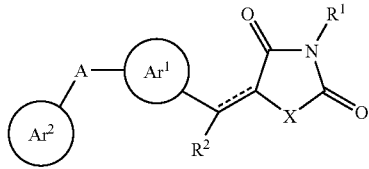
(IB)

or a pharmaceutically acceptable salt thereof, wherein

X is —S—;

R$^1$ is hydrogen, —C$_{1-4}$alkyl, —C$_{1-4}$alkyl-N(C$_{0-4}$alkyl)(C$_{0-4}$alkyl), —C$_{0-4}$alkyl-CO—N(C$_{0-4}$alkyl)(C$_{0-4}$alkyl), —C$_{0-4}$alkyl-CO—O(C$_{04}$alkyl), —C$_{1-4}$alkyl-piperidinyl, —C$_{1-4}$alkyl-morpholinyl, —C$_{1-4}$alkyl-pyrrolidinyl, —C$_{1-4}$alkyl-aryl, —C$_{1-4}$alkyl-aryl-aryl, optionally substituted with 1-6 independent halogen, —CN, —NO$_2$, —C$_{1-4}$alkyl, —O—C$_{1-4}$alkyl, —N(C$_{0-4}$alkyl)(C$_{0-4}$alkyl), —C$_{0-4}$alkyl-CO—O(C$_{0-4}$alkyl), —(C$_{0-4}$alkyl)-NH—CO—O(C$_{0-4}$alkyl), —(C$_{0-4}$alkyl)-CO—N(C$_{0-4}$alkyl)(C$_{0-4}$alkyl), —S(C$_{0-4}$alkyl), —S(O)(C$_{1-4}$alkyl), —SO$_2$(C$_{1-4}$alkyl), —SO$_2$N(C$_{0-4}$alkyl)(C$_{0-4}$alkyl), or —NHSO$_2$(C$_{1-4}$alkyl) substituents;

R$^2$ is —C$_{0-4}$alkyl;

Ar$^1$ is furyl optionally substituted with 1-2 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl), —CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl), —N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl—C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

Ar$^2$ is phenyl, pyridyl, pyriridinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$ alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

A is O, —S—, —CH—, —N(C$_{0-4}$alkyl), or absent;

wherein aryl independently is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-6 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$aalkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

M$^+$ is ammonium, sodium, lithium, potassium, calcium, magnesium, dicyclohexylamine, N-methyl-D-glucamine, arginine, or lysine; and any alkyl is optionally substituted with 1-6 independent halogen, phenyl, naphthyl, —N(C$_{0-4}$alkyl)(C$_{0-4}$alkyl), —C(O)—O(C$_{0-4}$alkyl), —CN, —NH—C(O)—O(C$_{0-4}$alkyl), —S(C$_{0-4}$alkyl), —NHSO$_2$(C$_{0-4}$alkyl)(C$_{0-4}$alkyl), or —SO$_2$N(C$_{0-4}$alkyl)(C$_{0-4}$alkyl) substituents.

In a second aspect, the compounds of the present invention are represented by Formula (IIA) or (IB):

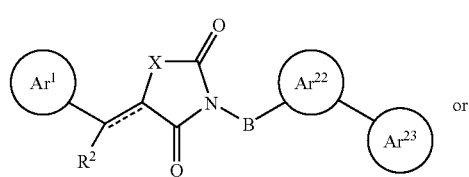

(IIA)

or

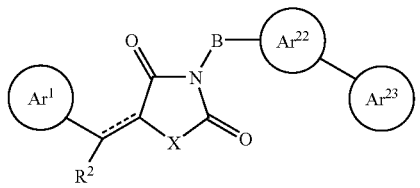

(IIB)

or a pharmaceutically acceptable salt thereof, wherein

X is —S—;

R$^2$ is —C$_{0-4}$alkyl;

Ar$^1$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

or optionally one of the substituents on Ar$^1$ is Ar$^2$, wherein Ar$^2$ is phenyl, pyridyl, pyriridinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-alkyl}$)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C═C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

B is —C$_{0-4}$alkyl-;

Ar$^{22}$ is phenyl optionally substituted with 1-4 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C═C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O—M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

Ar$^{23}$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C═C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O—M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

M$^+$ is ammonium, sodium, lithium, potassium, calcium, magnesium, dicyclohexylamine, N-methyl-D-glucamine, arginine, or lysine; and any alkyl is optionally substituted with 1-6 independent halogen, phenyl, naphthyl, —N(C$_{0-4}$alkyl)(C$_{0-4}$alkyl), —C(O)—O(C$_{0-4}$alkyl), —CN, —NH—C(O)—O(C$_{0-4}$alkyl), —S(C$_{0-4}$alkyl), —NHSO$_2$(C$_{0-4}$alkyl)(C$_{0-4}$alkyl), or —SO$_2$N(C$_{0-4}$alkyl)(C$_{0-4}$alkyl) substituents.

In an embodiment of this second aspect, the compounds of the present invention are represented by Formula (IIA) or (IIB):

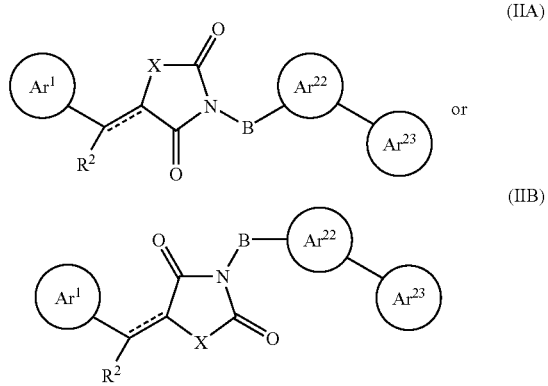

or a pharmaceutically acceptable salt thereof, wherein

X is —S—;

R$^2$ is —C$_{0-4}$alkyl;

Ar$^1$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)i-$_2$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

or optionally one of the substituents on Ar$^1$ is Ar$^2$, wherein Ar$^2$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$aalkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

B is —C$_{0-4}$alkyl-;

Ar$^{22}$ is phenyl optionally substituted with 1-4 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alklyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents;

Ar$^{23}$ is phenyl optionally substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

$M^+$ is ammonium, sodium, lithium, potassium, calcium, magnesium, dicyclohexylaamine, N-methyl-D-glucamine, arginine, or lysine; and any alkyl is optionally substituted with 1-6 independent halogen, phenyl, naphthyl, —N($C_{0-4}$alkyl)($C_{0-4}$alkyl), —C(O)—O($C_{0-4}$alkyl), —CN, —NH—C(O)—O($C_{0-4}$alkyl), —S($C_{0-4}$alkyl), —NHSO$_2$($C_{0-4}$alkyl)($C_{0-4}$alkyl), or —SO$_2$N($C_{0-4}$alkyl)($C_{0-4}$alkyl) substituents.

In another embodiment of this second aspect, the compounds of the present invention are represented by Formula (IIA) or (IIB):

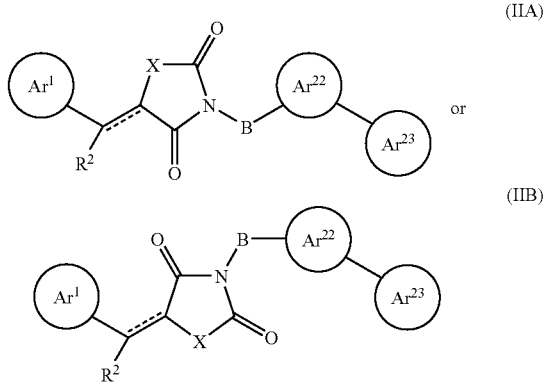

(IIA)

(IIB)

or a pharmaceutically acceptable salt thereof, wherein

X is —S—;

$R^2$ is —$C_{0-4}$alkyl;

$Ar^1$ is thienyl optionally substituted with 1-2 independent i) halogen, ii) —CN, iii) —NO$_2$, iv) —C v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —SO$_2$($C_{1-4}$alkyl), xiii) —SO$_2$N($C_{0-4}$alkyl)($C_{0-4}$alkyl), xiv) —NHSO$_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$alkyl)-, —C(O)—, —CH(OH)—, —C=C—, —C≡C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvii) —S(O)$_{1-2}$—($C_{1-6}$alkyl)-, xviii) —$C_{0-4}$alkyl-$C_{3-6}$cycloalkyl, or xix) —$C_{0-4}$alkyl-O—C(O)—$C_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

or optionally one of the substituents on $Ar^1$ is $Ar^2$, wherein $Ar^2$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —SO$_2$($C_{1-4}$alkyl), xiii) —SO$_2$N($C_{0-4}$alkyl)($C_{0-4}$alkyl), xiv) —NHSO$_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$alkyl)-, —C(O)—, —CH(OH)—, —C=C—, —C≡C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), xvii) —S(O)$_{1-2}$—($C_{1-6}$alkyl)-, xviii) —$C_{0-4}$alkyl-$C_{3-6}$cycloalkyl, or xix) —$C_{0-4}$alkyl-O—C(O)—$C_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

B is —$C_{0-4}$alkyl-;

$Ar^{22}$ is phenyl optionally substituted with 1-4 independent i) halogen, ii) —CN, iii) —NO$_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —SO$_2$($C_{1-4}$alkyl), xiii) —SO$_2$N($C_{0-4}$alkyl)($C_{0-4}$alkyl), xiv) —NHSO$_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$alkyl)-, —C(O)—, —CH(OH)—, —C=C—, —C≡C—, optionally substituted with 1-6 independent —CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-$M^+$, —OSO$_3$-$M^+$, —O—CO($C_{1-3}$alkyl)CO$_2$-$M^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvii) —S(O)$_{1-2}$—($C_{1-6}$alkyl)-, xviii) —$C_{0-4}$alkyl-$C_{3-6}$cycloalkyl, or xix) —$C_{0-4}$alkyl-O—C(O)—$C_{0-4}$alkyl, substituents;

$Ar^{23}$ is phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzofuryl, dibenzofuryl, benzthienyl, benzoxazolyl, benzothiazolyl, benzimidazolyl, pyridoimidazolyl, pyrimidoimidazolyl, pyridopyrazolyl, or pyrazolopyrimidinyl, any of which optionally is substituted with 1-5 independent i) halogen, ii) —CN, iii) —NO$_2$, iv) —CHO, v) —O—$C_{1-4}$alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$alkyl), ix) —($C_{0-4}$alkyl)-CO—N($C_{0-4}$alkyl)($C_{0-4}$alkyl), x) —S($C_{1-4}$alkyl), xi) —S(O)($C_{1-4}$alkyl), xii) —SO$_2$($C_{1-4}$alkyl), xiii) —SO$_2$N($C_{0-4}$alkyl)($C_{0-4}$alkyl), xiv) —NHSO$_2$($C_{1-4}$alkyl), xv) —$C_{1-10}$alkyl optionally substituted with 1-6 independent —CHO, —O—$C_{1-4}$alkyl, aryl, aryloxy-, —N($C_{0-6}$alkyl)($C_{0-6}$alkyl), —N($C_{0-6}$alkyl)-C(O)—($C_{0-6}$alkyl), —OPO(OH)O-M$^+$, —OSO$_3$-M$^+$, —O—CO($C_{1-3}$alkyl)CO$_2$-M$^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvi) —$C_{1-10}$alkyl in which one or more of the alkyl carbons is replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-, —C(O)—, —N($C_{0-6}$alkyl)-C(O)—N($C_{0-6}$alkyl)-, —C(O)—, —CH(OH)—, —C═C—, —C≡C—, optionally substituted with 1-6 independent CHO, aryl, aryloxy-, —N($C_{0-6}$alkyl)($C_{0-6}$alkyl), —N($C_{0-6}$alkyl)-C(O)—($C_{0-6}$alkyl), —OPO(OH)O-M$^+$, —OSO$_3$-M$^+$, —O—CO($C_{1-3}$alkyl)CO$_2$-M$^+$, —O—CO—($C_{1-6}$alkyl)-N($C_{0-6}$alkyl)($C_{0-6}$alkyl), —O—C(O)—$C_{0-6}$alkyl, —N($C_{0-6}$alkyl)-C(O)—N($C_{0-6}$alkyl)($C_{0-6}$alkyl), —O—C(O)—N($C_{0-6}$alkyl)($C_{0-6}$alkyl), —C(O)—N($C_{0-6}$alkyl)($C_{0-6}$alkyl), xvii) —S(O)$_{1-2}$—($C_{1-6}$alkyl)-, xviii) —$C_{0-4}$alkyl-$C_{3-6}$cycloalkyl, or xix) —$C_{0-4}$alkyl-O—C(O)—$C_{0-4}$alkyl substituents, or any two substituents optionally are joined to form a saturated ring having 5, 6, or 7 ring atoms, wherein 1 or 2 of the ring atoms are oxygen atoms and the remaining ring atoms are carbon;

M$^+$ is ammonium, sodium, lithium, potassium, calcium, magnesium, dicyclohexylamine, N-methyl-D-glucamine, arginine, or lysine; and any alkyl is optionally substituted with 1-6 independent halogen, phenyl, naphthyl, —N($C_{0-4}$alkyl)($C_{0-4}$alkyl), —C(O)—O($C_{0-4}$alkyl), —CN, —NH—C(O)—O($C_{0-4}$alkyl), —S($C_{0-4}$alkyl), —NHSO$_2$($C_{0-4}$alkyl)($C_{0-4}$alkyl), or —SO$_2$N($C_{0-4}$alkyl)($C_{0-4}$alkyl) substituents.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C═C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic substituent which is a single ring or multiple rings fused together. When formed of multiple rings, at least one of the constituent rings is aromatic. The preferred aryl substituents are phenyl and naphthyl groups.

The term "cycloalkyloxy" unless specifically stated otherwise includes a cycloalkyl group connected by a short $C_{1-2}$alkyl length to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the alkyl is a terminal group and is a direct bond when the alkyl is a bridging group.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five-member ring containing from 4 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "hetero$C_{0-4}$alkyl" means a heteroalkyl containing 3, 2, 1, or no carbon atoms. However, at least one heteroatom must be present. Thus, as an example, a hetero$C_{0-4}$alkyl having no carbon atoms but one N atom would be a —NH— if a bridging group and a —NH$_2$ if a terminal group. Analogous bridging or terminal groups are clear for an O or S heteroatom.

The term "amine" unless specifically stated otherwise includes primary, secondary and tertiary amines substituted with $C_{0-6}$alkyl.

The term "carbonyl" unless specifically stated otherwise includes a $C_{0-6}$alkyl substituent group when the carbonyl is terminal.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers unless specifically stated otherwise. It is understood that the dotted line in the above Formulas indicates an optional double bond at that site. When the indicated site just has a single bond, the presence of the required hydrogens is understood. When the site is a double bond, then cis/trans isomers are formed and are encompassed by this invention. When the site is a single bond, there can be four different substituents at one end of the bond in discussion. In such cases, diastereomers can arise and are encompassed by this invention.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above chemical Formulas are shown without a definitive stereochemistry at certain positions. The present invention includes all stereoisomers of the chemical Formulas and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula Ia, Ib, IIa, or IIb, (or pharmaceutically acceptable salts thereof) as an active ingredient, a pharmaceutically acceptable carrier and optionally other therapeutic ingredients or adjuvants. Such additional therapeutic ingredients include, for example, i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, and xiv) neurontin (gabapentin). The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The compositions are useful in the treatment of chronic, visceral, inflammatory and neuropathic pain syndromes. They are useful for the treatment of pain resulting from traumatic nerve injury, nerve compression or entrapment, postherpetic neuralgia, trigeminal neuralgia, diabetic neuropathy, chronic lower back pain, phantom limb pain, and pain resulting from cancer and chemotherapy, HIV and HIV treatment-induced neuropathy, chronic pelvic pain, neuroma pain, complex regional pain syndrome, chronic arthritic pain and related neuralgias. Compounds of this invention may also be utilized as local anesthetics. Compounds of this invention are useful in the treatment of irritable bowel syndrome and related disorders, as well as Crohn's disease.

Pharmaceutical compositions of the present invention have clinical uses in the treatment of epilepsy and partial and generalized tonic seizures. They are also useful for neuroprotection under ischaemic conditions caused by stroke or neural trauma and in patients with multiple sclerosis.

Pharmaceutical compositions of the present invention have clinical uses in the treatment of bipolar depression.

Pharmaceutical compositions of the present invention have clinical uses in the treatment of tachy-arrhythrias.

Further, it is understood that compounds of this invention can be administered at prophylactically effective dosage levels to prevent the above-recited conditions.

The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of inflammatory and neuropathic pain, or alternatively about 0.5 mg to about 7 g per patient per day. For example, inflammatory pain may be effectively treated by the administration of from about 0.01 mg to 75 mg of the compound per kilogram of body weight per day, or alternatively about 0.5 mg to about 3.5 g per patient per day. Neuropathic pain may be effectively treated by the administration of from about 0.01 mg to 125 mg of the compound per kilogram of body weight per day, or alternatively about 0.5 mg to about 5.5 g per patient per day. Further, it is understood that the compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula Ia, Ib, IIa, or IIb, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula Ia, Ib, IIa, or IIb, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula Ia, Ib, IIa, or IIb. The compounds of Formula Ia, Ib, IIa, or IIb, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula Ia, Ib, IIa, or IIb of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula Ia, Ib, IIa, or IIb, or pharmaceutically acceptable salts thereof, may also be prepared in powder or liquid concentrate form.

The compounds and pharmaceutical compositions of this invention have been found to block sodium channels. Accordingly, an aspect of the invention is a method of blocking sodium channels in a patient in need thereof comprising administering an effective amount of a compound of Formula Ia, Ib, IIa or IIb. Another aspect of the invention is the treatment in mammals of, for example, acute pain, chronic pain, visceral pain, inflammatory pain, or neuropathic pain—maladies that are amenable to amelioration through blockage of neuronal sodium channels—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the sodium channel blocking compound of this invention can be advantageously used in combination with i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, and xiv) neurontin (gabapentin).

The abbreviations used herein have the following tabulated meanings. Abbreviations not tabulated below have their meanings as commonly used unless specifically stated otherwise.

| Ac | Acetyl |
| AIBN | 2,2'-azobis(isobutyronitrile) |
| BINAP | 1,1'-bi-2-naphthol |
| Bn | Benzyl |
| CAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| Dppf | 1,1'-bis(diphenylphosphino)-ferrocene |
| EDCI | 1-(3-dimethylaminopropyl)-3-ethylcarbodiimide hydrochloride |

-continued

| $Et_3N$ | Triethylamine |
| GST | glutathione transferase |
| HMDS | Hexamethyldisilazide |
| LDA | lithium diisopropylamide |
| m-CPBA | metachloroperbenzoic acid |
| MMPP | monoperoxyphthalic acid |
| MPPM | monoperoxyphthalic acid, magnesium salt $6H_2O$ |
| Ms | methanesulfonyl = mesyl = $SO_2Me$ |
| Ms0 | methanesulfonate = mesylate |
| NBS | N-bromo succinimide |
| NSAID | non-steroidal anti-inflammatory drug |
| o-Tol | ortho-tolyl |
| OXONE ® | $2KHSO_5 \cdot KHSO_4 \cdot K_2SO_4$ |
| PCC | pyridinium chlorochromate |
| $Pd_2(dba)_3$ | Bis(dibenzylideneacetone) palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| r.t. | room temperature |
| Rac. | Racemic |
| SAM | aminosulfonyl or sulfonamide or $SO_2NH_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| $C_3H_5$ | Allyl |

ALKYL Group Abbreviations

| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | Cyclopentyl |
| c-Hex = | Cyclohexyl |

The following in vitro and in vivo assays were used in assessing the biological activity of the compounds described in this invention.

Compound Evaluation (In Vitro Assay):

The identification of inhibitors of the sodium channel is based on the ability of sodium channels to cause cell depolarization when sodium ions permeate through agonist-modified channels. In the absence of inhibitors, exposure of agonist-modified channel to sodium ions will cause cell depolarization. Sodium channel inhibitors will prevent cell depolarization caused by sodium ion movement through agonist-modified sodium channel. Changes in membrane potential can be determined with voltage-sensitive fluorescence resonance energy transfer (FRET) dye pairs that use two components, a donor coumarin ($CC_2DMPE$) and an acceptor oxanol (DiSBAC$_2$(3)). Oxanol is a lipophilic anion and distributes across the membrane according to membrane potential. In the presence of sodium channel agonist, but in the absence of sodium, the inside of the cell is negative with respect to the outside, oxanol is accumulated at the outer leaflet of the membrane and excitation of coumarin will cause FRET to occur. Addition of sodium will cause membrane depolarization leading to redistribution of oxanol to the inside of the cell, and, as a consequence, to a decrease in FRET. Thus, the ratio change (donor/acceptor) increases after membrane depolarization. In the presence of a sodium channel inhibitor cell depolarization will not occur, and therefore the distribution of oxanol and FRET will remain unchanged.

Cells stably transfected with the PN1 sodium channel (HEK-PN1) were grown in polylysine-coated 96-well plates at a density of ca. 140,000 cells/well. Media was aspirated, cells washed with PBS buffer, and incubated with 100 µL of 10 µM CC$_2$-DMPE in 0.02% pluronic acid. After incubation at 25° C. for 45 min, media was removed and cells were washed 2× with buffer. Cells were incubated with 100 µL of DiSBAC$_2$(3) in TMA buffer containing 20 µM veratridine, 20nM brevetoxin-3, and test sample. After incubation at 25° C. for 45 min in the dark, plates were placed in the VIPR instrument, and the fluorescence emission of both CC$_2$-DMPE and DiSBAC$_2$(3) recorded for 10 s. At this point, 100 µL of saline buffer was added to the wells to determine the extent of sodium-dependent cell depolarization, and the fluorescence emission of both dyes recorded for an additional 20 s. The ratio CC$_2$-DMPE/DiSBAC$_2$(3), before addition of saline buffer equals 1. In the absence of inhibitors, the ratio after addition of saline buffer is >1.5. When the sodium channel has been completely inhibited by either a known standard or test compound, this ratio remains at 1. It is possible, therefore, to titrate the activity of a sodium channel inhibitor by monitoring the concentration-dependent change in fluorescence ratio.

Electrophysiological Assays (In Vitro Assays):

Cell preparation: A HEK-293 cell line stably expressing the PN1 sodium channel subtype was established in-house. The cells were cultured in MEM growth media (Gibco) with 0.5 mg/mL G418, 50 units/mL Pen/Strep and 1 mL heat-inactivated fetal bovine serum at 37° C. and 10% CO$_2$. For electrophysiological recordings, cells were plated on 35 mm dishes coated with poly-D-lysine.

Whole-cell recordings: HEK-293 cells stably expressing the PN1 sodium channel subtype were examined by whole cell voltage clamp (Hamill et. al. Pfluegers Archives 391: 85-100 (1981)) using an EPC-9 amplifier and Pulse software (HEKA Electronics, Lamprecht, Germany). Experiments were performed at room temperature. Electrodes were fire-polished to resistances of 24 MΩ. Voltage errors were minimized by series resistance compensation, and the capacitance artefact was canceled using the EPC-9's built-in circuitry. Data were acquired at 50 kHz and filtered at 7-10 kHz. The bath solution consisted of 40 mM NaCl, 120 mM NMDG Cl, 1 mM KCl, 2.7 mM CaCl$_2$, 0.5 mM MgCl$_2$, 10 mM NMDG HEPES, pH 7.4, and the internal (pipet) solution contained 110 mM Cs-methanesulfonate, 5 mM NaCl, 20 mM CsCl, 10 mM CsF, 10 mM BAPTA (tetra Cs salt), 10 mM Cs HEPES, pH 7.4.

The following protocols were used to estimate the steady-state affinity of compounds for the resting and inactivated state of the channel ($K_r$ and $K_i$, respectively):

1) 8 ms testpulses to depolarizing voltages from −60 mV to +50 mV from a holding potential of −90 mV were used to construct current-voltage relationships (IV-curves). A voltage near the peak of the IV-curve (typically −10 or 0 mV) was used as the testpulse voltage throughout the remainder of the experiment.

2) Steady-state inactivation (availability) curves were constructed by measuring the current activated during an 8 ms testpulse following 10 s conditioning pulses to potentials ranging from −120 mV to −10 mV.

3) Compounds were applied at a holding potential at which 20-50% of the channels were inactivated and block was monitored during 8 ms test pulses at 2 s intervals.

4) After the compounds equilibrated, the voltage-dependence of steady-state inactivation in the presence of compound was determined (same protocol as 2) ). Compounds that block the resting state of the channel decrease the current elicited during testpulses from all holding potentials, whereas compounds that primarily block the inactivated state shift the mid-point of the steady-state inactivation curve. The maximum current at negative holding potentials ($I_{max}$) and the difference in the mid-points of the steady-state inactivation curves (ΔV) in control and in the presence of a compound were used to calculate $K_r$ and $K_i$ using the following equations:

$$K_r = \frac{[\text{Drug}] * I_{\text{Max},Drug}}{I_{\text{Max},Control} - I_{\text{Max},Drug}}$$

$$K_i = \frac{[\text{Drug}]}{\left(1 + \frac{[\text{Drug}]}{K_r}\right) * e^{\frac{-\Delta V}{k}} - 1}$$

In cases were the compound did not affect the resting state, $K_i$ was calculated using the following equation:

$$K_i = \frac{[\text{Drug}]}{e^{\frac{-\Delta V}{k}} - 1}$$

Rat Formalin Paw Test (In Vivo Assay):

Compounds were assessed for their ability to inhibit the behavioral response evoked by a 50 µL injection of formalin (5%). A metal band was affixed to the left hind paw of male Sprague-Dawley rats (Charles River, 200-250 g) and each rat was conditioned to the band for 60 min within a plastic cylinder (15 cm diameter). Rats were dosed with either vehicle or a test compound either before aocal) or after (systemic) formalin challenge. For local administration, compounds were prepared in a 1:4:5 vehicle of ethanol, PEG400 and saline (EPEGS) and injected subcutaneously into the dorsal surface of the left hind paw 5 min prior to formalin. For systemic administration, compounds were prepared in either a EPEGS vehicle or a Tween80 (10%)/sterile water (90%) vehicle and were injected i.v. (via the lateral tail vein 15 min after formnalin) or p.o. (60 min before formalin). The number of flinches was counted continuously for 60 min using an automated nociception analyzer (UCSD Anesthesiology Research, San Diego, Calif.). Statistical significance was determined by comparing the total flinches detected in the early (0-10 min) and late (11-60 min) phase with an unpaired t-test.

In Vivo Assay Using Rat CFA Model:

Unilateral inflammation was induced with a 0.2 ml injection of complete Freund's adjuvant (CFA: Mycobacterium tuberculosis, Sigma; suspended in an oil/saline (1:1) emulsion; 0.5 mg Mycobacterium/mL) in the plantar surface of the left hindpaw. This dose of CFA produced significant hind paw swelling but the animals exhibited normal grooming behavior and weight gain over the course of the experiment. Mechanical hyperalgesia was assessed 3 days after tissue injury using a Randall-Selitto test. Repeated Measures ANOVA, followed by Dunnett's Post Hoc test.

SNL: Mechanical Allodynia (In Vivo Assay)

Tactile allodynia was assessed with calibrated von Frey filaments using an up-down paradigm before and two weeks following nerve injury. Briefly, animals were placed in plastic cages with a wire mesh floor and allowed to acclimate for 15 min before each test session. To determine the 50% response threshold, the von Frey filaments (over a range of intensities from 0.4 to 28.8 g) were applied to the mid-plantar surface for 8 s or until a withdrawal response occurred. Following a positive response, an incrementally weaker stimulus was tested. If there was no response to a stimulus, then an incrementally stronger stimulus was presented. After the initial threshold crossing, this procedure was repeated for four stimulus presentations per animal per test session. Mechanical sensitivity was assessed 1 and 2 hr post oral administration of the test compound.

The compounds described in this invention displayed sodium channel blocking activity of <50 µM in the in vitro assays. It is preferred that the compounds display sodium channel blocking activity of <5 µM in the in vitro assays. It is more advantageous that the compounds display sodium channel blocking activity of <1 µM in the in vitro assays. It is even more advantageous that the compounds display sodium channel blocking activity of <0.5 µM in the in vitro assays. It is still more preferred that the compounds display sodium channel blocking activity of <0.1 µM in the in vitro assays.

Thus, because the compounds display sodium channel blocking activity of <5 µM in the in vitro assays, the compositions are useful in the treatment of chronic, visceral, inflammatory and neuropathic pain syndromes. They are useful for the treatment of pain resulting from traumatic nerve injury, nerve compression or entrapment, postherpetic neuralgia, trigeminal neuralgia, diabetic neuropathy, chronic lower back pain, phantom limb pain, and pain resulting from cancer and chemotherapy, HIV and HIV treatment-induced neuropathy, chronic pelvic pain, neuroma pain, complex regional pain syndrome, chronic arthritic pain and related neuralgias. Further, they are useful as local anesthetics. Compounds of this invention are useful in the treatment of irritable bowel syndrome and related disorders, as well as Crohns disease.

Pharmaceutical compositions of the present invention have clinical uses in the treatment of epilepsy and partial and generalized tonic seizures.

They are also useful for neuroprotection under ischaemic conditions caused by stroke or neural trauma and in patients with multiple sclerosis.

Pharmaceutical compositions of the present invention have clinical uses in the treatment of bipolar depression.

Pharmaceutical compositions of the present invention have clinical uses in the treatment of tachy-arrhythmias.

Further, it is understood that compounds of this invention can be administered at prophylactically effective dosage levels to prevent the above-recited conditions.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18-25° C. Evaporation of solvent was carried out using a rotary evaporator under reduced pressure (600-4000 pascals: 4.5-30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta ($\delta$) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in the above formulas except where defined otherwise.

The novel compounds of the present invention may be readily synthesized using techniques known to those skilled in the art, such described, for example, in *Advanced Organic Chemistry*, March, 4$^{th}$ Ed., John Wiley and Sons, New York, N.Y., 1992 ; *Advanced Organic Chemistry*, Carey and Sundberg, Vol. A and B, 3$^{rd}$ Ed., Plenum Press, Inc., New York, N.Y., 1990; *Protective groups in Organic Synthesis*, Green and Wuts, 2$^{nd}$ Ed., John Wiley and Sons, New York, N.Y., 1991; *Comprehensive Organic Transformations*, Larock, VCH Publishers, Inc., New York, N.Y., 1988 and references cited therein. The starting materials for the compounds described in this invention may be prepared using standard synthetic transformations of chemical precursors that are readily available from commercial sources, such as, Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Arcos, (Pittsburgh, Pa.) and Trans World Chemicals (Rockville, Md.).

The procedures described herein for synthesizing the compounds may include one or more steps of protecting group manipulations and various purification steps, such as, recrystallization, distillation, column chromatography, flash chromatography, thin-layer chromatography (TLC), radial chromatography and high-pressure chromatography (HPLC). The products can be characterized by using various techniques well known in chemical arts, such as, proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (LC-MS). Methods of protecting group manipulation, purification, structure identification and quantification are well know to one skilled in the art of chemical synthesis.

Compounds represented by formula IV (where $R_1$ is represented by a substituted aromatic ring, such as, phenyl, naphthyl, pyridyl, pyrimidyl, furyl and thienyl, and $R_2$, and $R_3$ are independently hydrogen or an alkyl or aryl group optionally substituted) can be prepared by reacting an appropriate aldehyde or ketone (II) with an appropriately substituted thiazolidindione (X=S), or its oxa-(X=O) analog under Knovenagel reaction conditions. The compounds of formula IV, where $R_3$ is hydrogen, can be reacted with an appropriate alkylating agent in the presence of a suitable base to provide the desired substituted compounds IV. The olefinic bond in compounds IV can be reduced under standard conditions to provide corresponding single bond analogs V (Scheme 1).

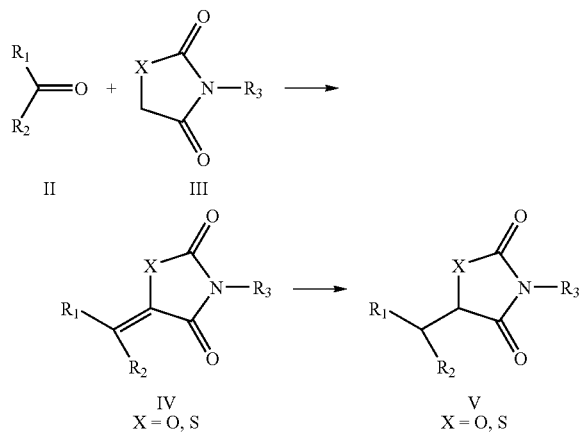

The aldehydes and ketones of Formula II used can either be purchased from commercial sources or can be prepared as outlined below in SCHEMES 2 and 3. The aldehydes or ketones of Formula VI can be prepared by reacting an appropriate phenol (VII) with VIII in an aprotic polar solvent, such as, DMF the presence of a base, such as, $K_2CO_3$ or $CS_2CO_3$ (SCHEME 2).

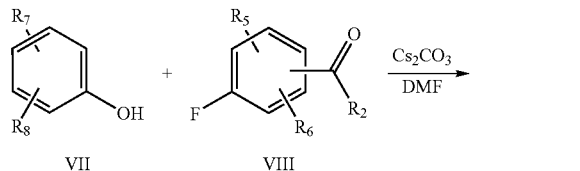

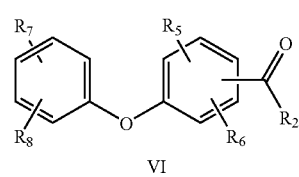

The compounds of formula IX can be prepared by the alkylation of a an appropriate phenol (X) with a substituted alkyl halide or benzyl halide as outlined below (SCHEME 3).

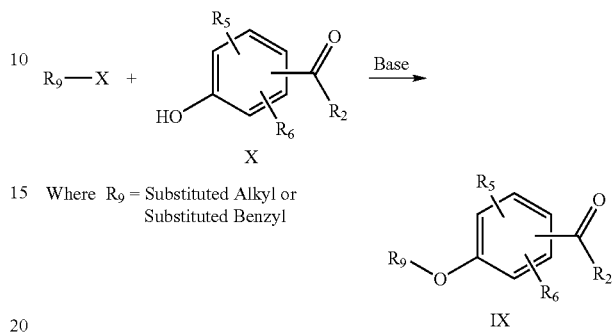

The aldehydes and ketones of formula XI, as shown below in SCHEME 4, can be prepared by transition metal catalyzed cross-coupling reactions, such as, for example, by Stille reaction, Suzuki reaction, or Heck reaction, of an appropriate organo boronic acid or an organo-tin compound (XII) with an aryl triflate or aryl halide (XIII). Similar reaction conditions can be utilized to assemble compounds of formula XV, where either A or B is an appropriately substituted 5- or 6-membered heteroaromatic ring. Furthermore, compounds of formula XV in which both A and B are heteroaromatic rings can also be synthesized by applying similar reaction conditions.

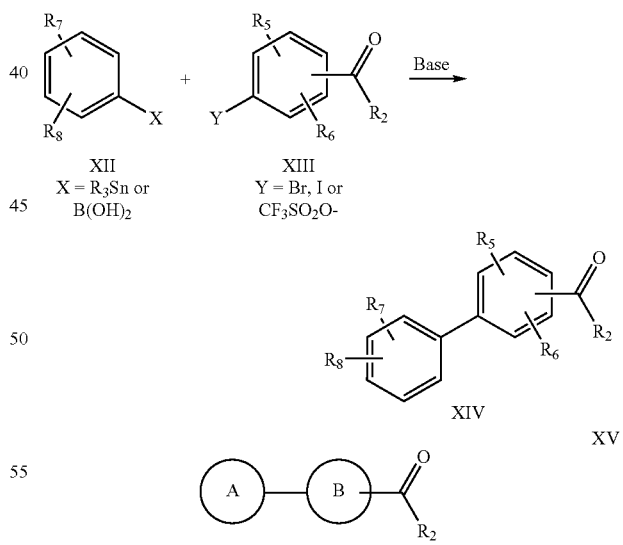

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, calcium hydroxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate, sodium carbonate, Cesium carbonate, sodium hydrogen carbonate, cesium hydrogen carbonate, alkali metal alkoxides and alkaline earth metal alkoxides such as sodium methoxide, sodium ethoxide, potassium tert-butoxide and magnesium ethoxide, alkali metal alkyls such as methyllithium, n-butyllithium, sec-butyllithium, t-bultyllithium, phenyllithium, alkyl magnaesium halides, organic bases such as trimethylamine, triethylamine, triisopropylamine, N,N-diisopropylethylamine, piperidine, N-methyl piperidine, morpholine, N-methyl morpholine, pyridine, collidines, lutidines, 4-dimethylaminopyridine and also bicyclic amines such as DBU and DABCO.

As described previously, in preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, histone deacetylase inhibitors may also be administered by controlled release means and/or delivery devices.

EXAMPLE 1

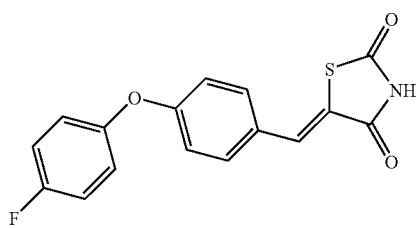

(5Z)-5-[4-(4-fluorophenoxy)benzylidene]-1,3-thiazolidine-2,4-dione

Step A: Preparation of 4-(4-fluorophenoxy)benzaldehyde

To a solution of 4-fluorophenol (1.06 g) in anhydrous DMF (10 mL) were added anhydrous potassium carbonate (2.07 g) and 4-fluorobenzaldehyde (1.2 g) at room temperature. The reaction was stirred at 100° C. for 16 h, then cooled to room temperature and diluted with ether. The organic layer was washed with 1N sodium hydroxide, and then with water, dried over sodium sulphate, and concentrated under reduced pressure. The crude aldehyde obtained was purified by flash-column chromatography on silica-gel using 20% EtOAc in hexanes to provide the pure aldehyde.

Step B: Coupling of 2,4-thiazolidinedione to aldehyde

To a solution of 4-(4-fluorophenoxy)benzaldehyde (0.54 g, 2.5 mMol) and 2,4-thiazolidinedione (0.352 g, 3 mMol) in toluene (20 mL) were added piperidine (0.032 mL, 0.325 mMol) and benzoic acid (0.046 mg, 0.375 mMol). The reaction was refluxed for 4 h with continuous removal of water. The reaction was cooled and filtered. The crystalline product collected was washed with petroleum ether on the filter and dried in vacuo.
$^1$H NMR (DMSO-d$_6$): δ 7.75(s, 1H), 7.61(d, J=8.7 Hz, 2H), 7.28-7.18 (m, 4H), 7.08 (d, J=8.7 Hz, 2H,). MS (ESI): m/e 316 (M+1)$^+$

EXAMPLE 2

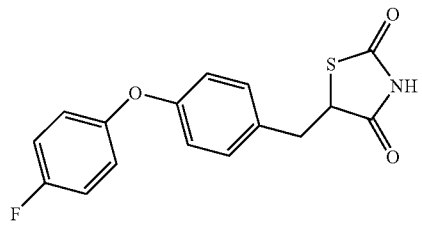

5-[4-(4-fluorophenoxy)benzyl]-1,3-thiazolidine-2,4-dione

Magnesium turnings (0.281 g) was added to a solution of 5-(4-(4-fluorophenoxy)benzyl)thiazolidine-2,4-dione (0.204 g) in anhydrous methanol (5.3 mL), and the resulting mixture was stirred at 45° C. for 8 h. The mixture was cooled to 0° C. and acidified with 6N HCl to pH 5.0, then extracted with ethyl acetate. The organic phase was washed with water, dried (Na$_2$SO$_4$) and concentrated. The crude material was purified by preparative thin-layer chromatography using EtOAc-hexanes (3:2) to give the titled product.
$^1$HNMR (CDCL$_3$): δ0 8.44(bs, 1H), 7.20(d, J=8.5 Hz, 2H), 7.06-7.04 (m, 2H), 7.01-6.99 (m, 2H), 6.93 (d, J=8.7 Hz, 2H,), 4.54 (m, 1H), 3.50 (m, 1H), 3.16 (m, 1H). MS (ESI): m/e 318 (M+1)$^+$

EXAMPLE 3

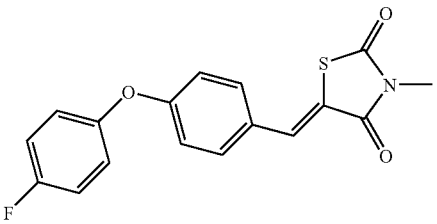

(5Z)-5-[4-(4-fluorophenoxy)benzylidene]-3-methyl-1,3-thiazolidine-2,4-dione

To a solution of 5-(4-(4-fluorophenoxy)benzylidene)thiazolidine-2,4-dione (0.055 g) in a 1:1 mixture of THF and DMF (1.6 mL) was added anhydrous K$_2$CO$_3$ (0.022 g). To the well stirred resulting homogeneous mixture, methyl iodide (0.5 mL) was added and the reaction was stirred overnight at room temperature. The reaction was diluted with ice-water, extracted with EtOAc, and the organic layer was washed with water, dried (Na$_2$SO$_4$) and concentrated in vacuo to give the titled compound.

$^1$HNMR (CDCL$_3$): δ 8.03 (s, 1H), 7.49 (d, J=8.7 Hz, 2H), 7.12-7.02 (m, 6H), 3.26 (s, 3H). MS (ESI): m/e 330(M+1)$^+$

EXAMPLE 4

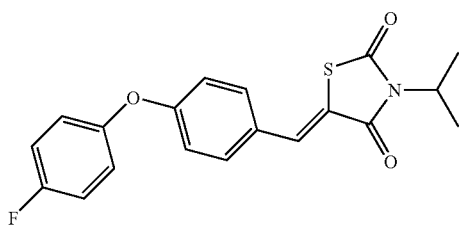

(5Z)-5-[4-(4-fluorophenoxy)benzylidene]-3-isopropyl-1,3-thiazolidine-2,4-dione

The titled compound was prepared by the alkylation of 5-(4-(4-fluorophenoxy)benzylidene)thiazolidine-2,4-dione with 2-iodopropane employing the reaction conditions described in EXAMPLE 3.

$^1$HNMR (CDCL$_3$): δ 7.82 (s, 1H), 7.64(d, J=8.9 Hz, 2H), 7.24-7.1 (m, 4H), 7.11 (d, J=8.9 Hz, 2H,), 4.64 (m, 1H), 1.46 (d, J=6.8 Hz, 6H). MS (ESI): m/e 358 (M+1)$^+$

EXAMPLE 5

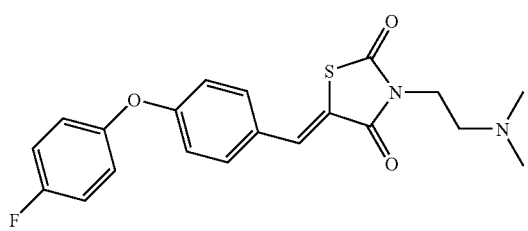

(5Z)-3-[2-(diimethylamino)ethyl]-5-[4-(4-fluorophenoxy)benzylidene]-1,3-thiazolidine-2,4-dione To a solution of 5-(4-(4-fluorophenoxy)benzylidene)thiazolidine-2,4-dione (0.05 g) in a 1:1 mixture of THF and DMF (1.6 mL) was added anhydrous K$_2$CO$_3$ (0.044 g). To the well stirred homogeneous mixture was added 2-chloro-N,N-dimethylaminoethane (0.04 g) and stirred overnight at room temperature. The reaction was diluted with ice-water, extracted with EtOAc, and the organic layer was washed with water, dried (Na$_2$SO$_4$) and concentrated in vacuo to give the titled compound.

$^1$HNMR (CD$_3$)$_2$CO): δ 7.86 (s, 1H), 7.66 (d, J=8.7 Hz, 2H), 7.26-7.12 (m, 4H), 7.10 (d, J=8.7 Hz, 2H,), 3.84 (t, J$_1$=12.8 Hz, J$_2$=6 Hz, 2H), 2.56 (t, J$_1$=12.8 Hz, J$_2$=6 Hz, 2H), 2.22 (s, 6H). MS (ESI): m/e 387.2 (M+1)$^+$

EXAMPLE 6

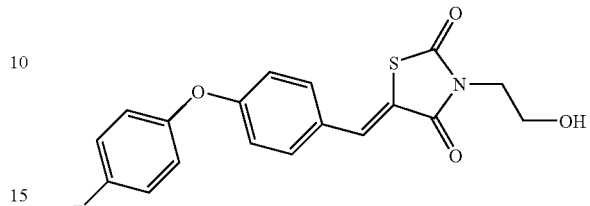

(5Z)-5-[4-(4-fluorophenoxy)benzylidene]-3-(2-hydroxyethyl)-1,3-thiazolidine-2,4-dione To a solution of 5-(4-(4-fluorophenoxy)benzylidene)thiazolidine-2,4-dione (0.05 g) in a 1:1 mixture of ThF and DMF (1.6 mL) was added anhydrous K$_2$CO$_3$ (0.022 g). To the well stirred homogeneous mixture was added 2-chloro-ethanol (0.04 g) and stirred overnight at room temperature. The reaction was diluted with ice-water, extracted with EtOAc, and the organic layer was washed with water, dried (Na$_2$SO$_4$) and concentrated in vacuo to give the titled compound.

$^1$HNMR (CDCL$_3$): δ 7.89 (s, 1H), 7.48 (d, J=8.7 Hz, 2H), 7.12-7.02 (m, 6H), 3.99(m, 2H), 3.90 (m, 2H). MS data: m/e 360(M+1)$^+$

EXAMPLE 7

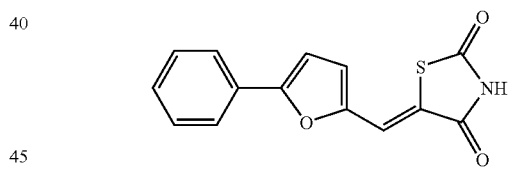

(5Z)-5-[(5-phenyl-2-furyl)methylene]-1,3-thiazolidine-2,4-dione

To a solution of PhB(OH)$_2$ (0.13 g) and 5-bromofurfural (0.17 g) in n-propanol (5 mL) were added Pd(OAC)$_2$ (10 mg) and Ph$_3$P (50 mg) under nitrogen followed by 2M Na$_2$CO$_3$ (0.3 mL) and water (0.1 mL). The mixture was refluxed for 4 h. The reaction was cooled to rt, diluted with water and extracted with EtOAC. The organic phase was washed with 1N NaOH followed by water, and then dried (Na$_2$SO$_4$). The desired compound 5-phenyl-furan-2-aldehyde was obtained as oil after purification by radial chromatography using 2% EtOAC/hexanes. The aldehyde, thus obtained, was condensed with 2,4-thiazolidinedione using the reaction condition described in Step B of EXAMPLE 1 to give the titled product as a foam.

$^1$HNMR (CDCL$_3$): δ 7.86-76. (m, 5H), 7.7 (s, 1H), 7.51 (d, J=3.9 Hz, 1H), 7.27 (d, J=3.9 Hz, 1H). MS data: m/e 271 and 273(M+1)$^+$

EXAMPLE 8

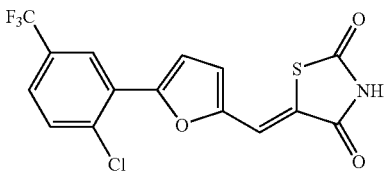

(5Z)-5-({5-[2-chloro-5-(trifluoromethyl)phenyl]-2-furyl}methylene)-1,3-thiazolidine-2,4-dione The titled compound was prepared by the condensation of 5-(2-chloro-5-trifluoromethylphenyl)furan-2-aldehyde (1g) [prepared by the condensation of (2-chloro-5-trifluoromethyl)phenyl boronic acid with 2-bromo-furfural] with 2,4-thiazolidinedione (0.52 g) under the reaction condition described in Step B of EXAMPLE 1.

$^1$HNMR (CD$_3$)$_2$CO): δ 8.29 (s, 1H), 7.85 (d, J=8.4 Hz, 1H), 7.76 (d, J=8.4 Hz, 1H), 7.7 (s, 1H), 7.51 (d, J=3.9 Hz, 1H), 7.27 (d, J=3.9 Hz, 1H). MS data: m/e 374.0(M+1)$^+$

EXAMPLE 9

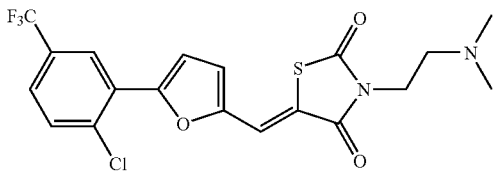

(5Z)-5-({5-[2-chloro-5-(trifluoromethyl)phenyl]-2-furyl}methylene)-3-[2-(dimethylamino)ethyl]-1,3-thiazolidine-2,4-dione The titled compound was prepared by the reaction of 5-(5-(2-Chloro-5-trifluoromethyl phenyl)furylidene)thiazolidine-2,4-dione (0.19 g) with 2-chloro-N,N-dimethylamino ethane (0.12 g) in the presence of Cs$_2$CO$_3$ (0.35 g) using the procedure described in EXAMPLE 5.

$^1$HNMR (CD$_3$)$_2$CO): δ 8.29 (s, 1H), 7.85 (d, J=8.4 Hz, 1H), 7.76 (d, J=8.4 Hz, 1H), 7.77 (s, 1H), 7.57 (d, J=3.9 Hz, 1H), 7.27 (d, J=3.9 Hz, 1H), 3.85 (t, J1=12 Hz, J2=6.4 Hz, 2H), 2,56 (bt, J$_1$=12 Hz, J$_2$=6.4 Hz, 2H), 2.23 (s, 6H). MS data: m/e 445.1(M+1)$^+$

EXAMPLE 10

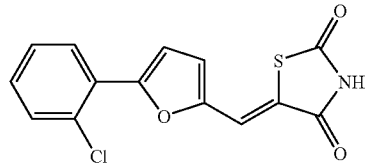

(5Z)-5-{[5-(2-chlorophenyl)-2-furyl]methylene}-1,3-thiazolidine-2,4-dione

The titled compound was prepared by the condensation of 5-(5-(2-chloro-phenyl)furan-2-aldehyde (1.0 g) with 2,4-thiazolidinedione (0.68 g) using the procedure described in Step B of EXAMPLE 1.

$^1$HNMR ([DMSO-d$_6$]): δ 7.90 (d, J=6.7 Hz, 1H), 7.66 (s, 1H), 7.61 (m, 1H), 7.56 (t, J$_1$=15.4 Hz, J$_2$=7.7 Hz, 1H), 7.44 (m, 1H), 7.40 (d, J=3.7 Hz, 1H), 7.25 (d, J=3.7 Hz, 1H). MS data: m/e 306.2 (M+1)$^+$

EXAMPLE 11

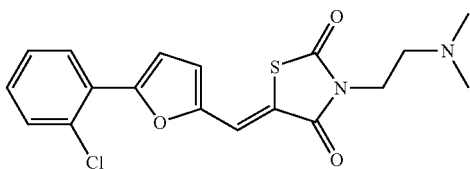

(5Z)-5-{([5-(2-chlorophenyl)-2-furyl]methylene}-3-[2-(dimethylamino)ethyl]-1,3-thiazolidine-2,4-dione The titled compound was prepared by the reaction of 5-(5-(2-chlorophenyl)furylidene)thiazolidine-2,4-dione with 2-chloro-N,N-dimethylamino ethane in the presence of Cs$_2$CO$_3$ using the condition described in EXAMPLE 5.

$^1$HNMR (CD$_3$)$_2$CO): δ 8.06 (d, J=1.6 Hz, 1H), 7.77 (s, 1H), 7.65-7.48 (m, 2H), 7.47-7.44 (m, 2H), 7.27 (d, J=3.7 Hz,1H), 3.86 (t, J=6.4 Hz, 2H), 2.63 (t, J=6.4 Hz, 2H), 2.28 (s, 6H). MS data: m/e 377.1 (M+1)$^+$ Other EXAMPLES of this invention, prepared using the condition similar to that described in EXAMPLE 5, are shown below in TABLE 1:

TABLE 1

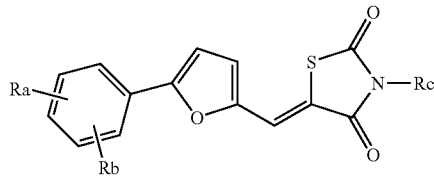

| EX. | R$_a$ | R$_b$ | R$_c$ | MS Data (m/e, M + 1) |
|---|---|---|---|---|
| 12 | 3-Cl | H | H | 306.0 |
| 13 | 3-Cl | H | (CH$_3$)$_2$N—CH$_2$—CH$_2$ | 377.15 |
| 14 | 2-CH$_3$ | H | (CH$_3$)$_2$N—CH$_2$—CH$_2$ | 357.2 |
| 15 | 2-Cl | 5-CF$_3$ | (CH$_3$)$_3$N$^+$—CH$_2$—CH$_2$ | 459.1 |
| 16 | 4-F | H | (CH$_3$)$_2$N—CH$_2$—CH$_2$ | 361.1 |
| 17 | 2-NO$_2$ | H | (CH$_3$)$_2$N—CH$_2$—CH$_2$ | 388.1 |
| 18 | 2-Cl | H | CH$_3$OOC—CH$_2$ | 378.1 |
| 19 | 2-Cl | H | NH$_2$OC—CH$_2$ | 363.1 |
| 20 | 2-Cl | H | HO—CH$_2$—CH$_2$ | 350.1 |
| 21 | 3-NO$_2$ | H | H | 317 |
| 22 | 4-NO$_2$ | H | H | 317 |
| 23 | 2-NO$_2$ | H | H | 317 |
| 24 | 2-CH$_3$O | H | H | 302 |
| 25 | 3-CH$_3$O | H | H | 302 |
| 26 | 4-CH$_3$O | H | H | 302 |
| 27 | 2-F | H | H | 290.1 |
| 28 | 4-Cl | H | H | 306 |
| 29 | 2-CF$_3$ | H | H | 340 |
| 30 | 2-Cl | H | 2-thiazolyl | 389 |
| 31 | 2-Cl | H | (5-NO$_2$)furylmethyl | 431.3 |
| 32 | 2-Cl | H | CH$_3$ | 320 |
| 33 | 2-CF$_3$O | H | H | 366.1 |
| 34 | 2-CF$_3$CH$_2$O | H | H | 379.9 |

EXAMPLE 35

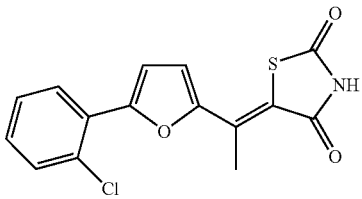

(5Z)-5-{1-5-(2-chlorophenyl)-2-furyl]ethylidene}-1,3-thiazolidine-2,4-dione 5-(2-chlorophenyl)furyl-2-ethaone was prepared by the coupling reaction of 2-chlorophenyl boronic acid (0.31 g) with 2-bromo-5-acetyl furan (0.37 g) using the procedure described in EXAMPLE 15. The ketone (0.129 g), thus obtained, was then condensed with 2,4-thiazolidine-2,4dion (28 mg) in the presence of benzoic acid (10.7 mg) and piperidine (0.0075 mL) under the conditions described in EXAMPLE 5 to give the titled compound.

$^1$HNMR (CD$_3$Cl$_3$): δ 8.06 (d, J=1.6 Hz, 1H), 7.77 (s, 1H), 7.65-7.48 (m, 2H), 7.47-7.44 (m, 2H), 7.27 (d, J=3.7 Hz, 1H), 2.76 (s, 3H). MS data: m/e 319.95 (M+1)$^+$ Other EXAMPLES of this invention, prepared using the condition similar to that described in EXAMPLE 5, are shown below in TABLE 2:

TABLE 2

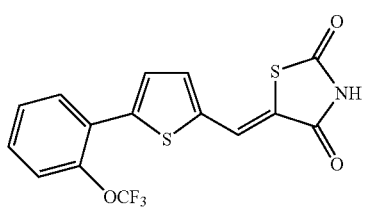

| EX. | R$_a$ | R$_b$ | R | MS data (m/e, M + 1) |
|---|---|---|---|---|
| 36 | 2-Cl | 5-CF$_3$ | —SO$_2$NHC(CH$_3$)$_3$ | 619 |
| 37 | 2-Cl | 5-CF$_3$ | —SO$_2$NH$_2$ | 619 |
| 38 | 3-Cl | H | —SO$_2$NHC(CH$_3$)$_3$ | 551 |
| 39 | 3-Cl | H | —SO$_2$NH$_2$ | 551.1 |
| 40 | 2-Cl | H | —SO$_2$NHC(CH$_3$)$_3$ | 551 |
| 41 | 2-Cl | H | —SO$_2$NH$_2$ | 551.1 |
| 42 | 2-NO$_2$ | H | —SO$_2$NH$_2$ | 562 |

EXAMPLE 43

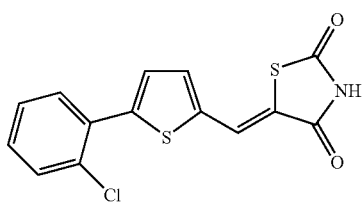

(5Z)-5-{[5-(2-chlorophenyl)thien-2-yl]methylene}-1,3-thiazolidine-2,4-dione

To a solution of 2-chloro-1-iodobenzene (0.25 mL) and 5-formyl-2-thiophene boronic acid (0.385 g) in DME (8 mL) were added Pd(OAc)$_2$ (0.009 g) and Ph$_3$P (0.021 g) followed by 2M sodium carbonate (1 mL). The mixture was stirred at rt for 1 h. The reaction was diluted with ethylacetate (20 mL) and washed with water and brine, and then dried (sodium sulfate). The crude product was purified by flash-chromatography using EtOAc-hexanes (1:5) to give the desired 5-(2-chlorophenyl)thiophene-2-aldehyde as an oil. The aldehyde (0.15 g), thus obtained, was then condensed with 2,4-thiazolidine-2,4dione in the presence of benzoic acid and piperidine under the conditions described in EXAMPLE 5 to give the title compound 5-(5-(2-chloro-phenyl)thienylidene)thiazolidine-2,4-dione.

$^1$HNMR (CD$_3$Cl$_3$): δ 8.05 (s, 1H), 7.62-7.60 (m, 1H), 7.57-7.55 (m, 1H), 7.51 (d, J=3.8 Hz, 1H), 7.45 (d, J=3.8 Hz, 1H), 7.38 (m, 2H). MS data: m/e 321.8 (M+1)$^+$

EXAMPLE 44

(5Z)-5-({5-[2-(trifluoromethoxy)phenyl]thien-2-yl}methylene)-1,3-thiazolidine-2,4-dione To a solution of 2-trifluoromethoxy-1-bromobenzene (0.21 mL) and 5-formyl-2-thiophene boronic acid (0.23 g) in DME (11 mL) were added Pd(OAc)$_2$ (0.014 g) and Ph$_3$P (0.033 g) followed by 2M sodium carbonate (1 mL) and water (1 mL). The mixture was stirred at rt for 3 h. The reaction was diluted with ethylacetate (20 mL) and washed with water and brine, and then dried (sodium sulfate). The crude product was purified by flash-chromatography using acetone-hexanes (1:4) to give the desired 5-(2-trifluoromethoxyphenyl)thiophene-2-aldehyde as an oil [MS data: m/e 273 (M+1)$^+$]. The aldehyde (0.15 g), thus obtained, was then condensed with 2,4-thiazolidine-2,4-dione in the presence of benzoic acid and piperidine under the conditions described in EXAMPLE 5 to give the title compound 5-(5-(2-trifluoromethoxyphenyl)thienylidene)thiazolidine-2,4-dione.

$^1$HNMR (CD$_3$Cl$_3$): δ 7.68 (s, 1H), 7.50-7.48 (m, 1H), 7.29 (s, 1H), 7.26 (d, J=4.1 Hz, 1H), 7.185 (d, J=4.1 Hz, 1H), 7.17-7.12 (m, 2H). MS data: m/e 372 (M+1)$^+$

EXAMPLE 45

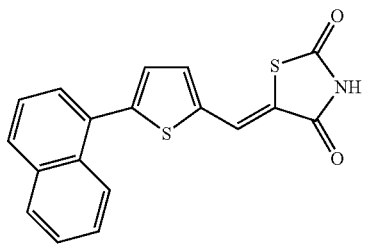

(5Z)-5-{[5-(1-naphthyl)thien-2-yl]methylene}-1,3-thiazolidine-2,4-dione

To a solution of naphthyl-1-boronic acid (0.21 mg) and 5-bromo-2-thiophene aldehyde (0.15 mL) in DME (10 mL) were added Pd(OAc)$_2$ (0.008 g) and Ph$_3$P (0.018 g) followed by 2M sodium carbonate (1 mL) and water (1 mL). The mixture was stirred at rt for 3 h. The reaction was diluted with ethylacetate (20 mL) and washed with water and brine, and then dried (sodium sulfate). The crude product was purified by flash-chromatography using acetone-hexanes (1:4) to give the desired 5-(1-naphthyl)thiophene-2-aldehyde as an oil [MS data: m/e 239 (M+1)$^+$]. The aldehyde (0.15 g), thus obtained, was then condensed with 2,4-thiazolidine-2,4-dione in the presence of benzoic acid and piperidine under the conditions described in EXAMPLE 5 to give the title compound 5-(5-(1-naphthyl)thienylidene)thiazolidine-2,4-dione.

$^1$HNMR (CD$_3$Cl$_3$): δ 8.22-8.20 (m, 1H), 8.09 (s, 1H), 7.98-7.92 (m, 2H), 7.66-7.62 (m, 1H), 7.60-7.54 (m, 2H), 7.29 (s, 1H), 7.53 (d, J=3.9 Hz, 1H), 7.39 (d, J=3.9 Hz, 1H). MS data: m/e 337.8 (M+1)$^+$ Other EXAMPLES of this invention are shown below in TABLE 3:

TABLE 3

| EX. | R$_d$ | R | MS (m/e, M + 1) |
|---|---|---|---|
| 46 | 5-Cl | —SO$_2$NHC(CH$_3$)$_3$ | 491.1 |
| 47 | 5-Cl | —SO$_2$NH$_2$ | 491.1 |
| 48 | 5-(2-Thienyl)- | —SO$_2$NHC(CH$_3$)$_3$ | 539.1 |
| 49 | 5-(2-Thienyl)- | —SO$_2$NH$_2$ | 539.1 |

Other EXAMPLES of this invention are shown below in TABLE 4:

TABLE 4

| EX. | R$_d$ | R$_c$ | MS Data (m/e, M + 1) |
|---|---|---|---|
| 50 | 5-(2-Thienyl)- | H | 294.1 |
| 51 | 4-(2-Cl-Phenyl)- | H | 321.8 |

EXAMPLE 52

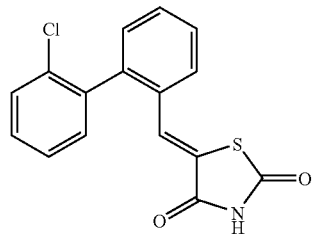

(5Z)-5-[(2'-chloro-1,1'-biphenyl-2-yl)methylene]-1,3-thiazolidine-2,4-dione

Step A: Preparation of 2-formyl-(2'-chloro-1,1'-biphenyl)

To a solution of 2-bromochlorobenzene (0.12 mL, 1 mmol) and 2-formylbenzeneboronic acid (0.17 g, 1.1 mmol) in toluene (9 mL) were added 2M aq. sodium carbonate (1.2 mL) followed by (Ph$_3$P)$_4$Pd (0.34 g, 0.3 mmol). The resulting reaction mixture was refluxed for 3 h, cooled and diluted ethyl acetate. The organic phase was washed with water, saturated aq. sodium bicarbonate, brine and dried over sodium sulfate. The filtrate was concentrated in vacuo and the residue obtained was purified by chromatography (hexane:ethyl acetate; 4:1) to yield the title product.

MS data: m/e 217.1 (M+1)$^+$

Step B: 5-(2-(2-chlorophenyl)benzylidene)thiazolidine-2,4-dione

To a solution of 2-formyl-(2'-chloro-1,1'-biphenyl) (0.12 g, 0.55 mmol) and 2,4-thiazolidinedione (0.08 g, 0.65 mmol) in toluene (10 mL) were added piperidine (0.008 mL, 0.073 mMol) and benzoic acid (0.011 mg, 0.08 mmol), and the reaction was refluxed for 4 h with continuous removal of water. The solvent was then distilled off and the oily residue obtained was purified by chromatography on silica-gel using hexane: ethyl acetate (3:1) as the eluent to yield titled product.

$^1$H NMR (DMSO-d$_6$): δ 7.75(s, 1H), 7.61 (d, J=8.7 Hz, 2H), 7.28-7.18 (m, 4H), 7.08 (d, J=8.7 Hz, 2H,). MS data: m/e 315.95 (M+1)$^+$

EXAMPLE 53

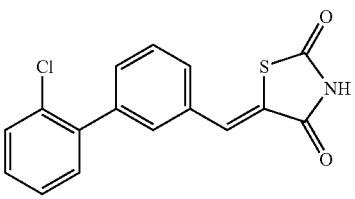

(5Z)-5-[(2'-chloro-1,1'-biphenyl-3-yl)methylene]-1,3-thiazolidine-2,4-dione

Step A: Preparation of 3-formyl-(2'-chloro-1,1'-biphenyl)

To a solution of 2-bromochlorobenzene (0.24 mL, 2 mmol) and 3-formylbenzeneboronic acid (0.35 g, 2.2 mmol) in toluene (20 mL) were added 2M aq. sodium carbonate (2.6 mL) followed by (Ph₃P)₄Pd (0.34 g, 0.3 mmol). The resulting reaction mixture was refluxed for 3 h, cooled and diluted ethyl acetate. The organic phase was washed with water, saturated aq. sodium bicarbonate, brine and dried over sodium sulfate. The filtrate was concentrated in vacuo and the residue obtained was purified by chromatography (hexane:ethyl acetate; 4:1) to yield the title product.

¹HNMR (CDCl₃)(δ, ppm): 8.06 (d, 2H), 7.58 (d, 2H), 7.54-7.52 (m, 1H), 7.38-7.35 m, 3H), 2.68 (s, 3H) MS data: m/e 217 (M+1)⁺

Step B: 5-(3-(2-chlorophenyl)benzylidene)thiazolidine-2,4-dione

To a solution of 3-formyl-(2'-chloro-1,1'-biphenyl) (0.12 g, 0.55 mmol) and 2,4-thiazolidinedione (0.08 g, 0.65 mmol) in toluene (10 mL) were added piperidine (0.008 mL, 0.073 mMol) and benzoic acid (0.011 mg, 0.08 mmol), and the reaction was refluxed for 4 h with continuous removal of water. The solvent was then distilled off and the oily residue obtained was purified by chromatography on silica-gel using hexane: ethyl acetate (3:1) as the eluent to yield titled product.

¹H NMR (DMSO-d₆): δ 7.75(s, 1H), 7.61(d, J=8.7 Hz, 2H), 7.28-7.18 (m, 4H), 7.08 (d, J=8.7 Hz, 2H,). MS data: m/e 315.9 (M+1)⁺

EXAMPLE 54

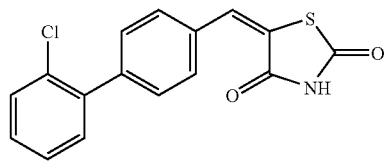

(5E)-5-[(2'-chloro-1,1'-biphenyl-4-yl)methylene]-1,3-thiazolidine-2,4-dione

Step A: Preparation of 4-formyl-(2'-chloro-1,1'-biphenyl)

To a solution of 2-bromochlorobenzene (0.24 mL, 2 mmol) and 4-formylbenzeneboronic acid (0.35 g, 2.2 mmol) in toluene (20 mL) were added 2M aq. sodium carbonate (2.6 mL) followed by (Ph₃P)₄Pd (0.34 g, 0.3 mmol). The resulting reaction mixture was refluxed for 3 h, cooled and diluted ethyl acetate. The organic phase was washed with water, saturated aq. sodium bicarbonate, brine and dried over sodium sulfate. The filtrate was concentrated in vacuo and the residue obtained was purified by chromatography (hexane:ethyl acetate; 4:1) to yield the title product.

¹HNMR (CDCl₃)(δ, ppm): 8.06 (d, 2H), 7.58 (d, 2H), 7.54-7.52 (m, 1H), 7.38-7.35 m, 3H), 2.68 (s, 3H) MS data: m/e 217 (M+1)⁺

Step B: 5-(4-(2-chlorophenyl)benzylidene)thiazolidine-2,4-dione

To a solution of 4-formyl-(2'-chloro-1,1'-biphenyl) (0.12 g, 0.55 mmol) and 2,4-thiazolidinedione (0.08 g, 0.65 mmol) in toluene (10 mL) were added piperidine (0.008 mL, 0.073 mMol) and benzoic acid (0.011 mg, 0.08 mmol), and the reaction was refluxed for 4 h with continuous removal of water. The solvent was then distilled off and the oily residue obtained was purified by chromatography on silica-gel using hexane: ethyl acetate (3:1) as the eluent to yield titled product.

¹H NMR (DMSO-d₆): δ 7.75(s, 1H), 7.61(d, J=8.7 Hz, 2H), 7.28-7.18 (m, 4H), 7.08 (d, J=8.7 Hz, 2H,). MS data: m/e 315.9 (M+1)⁺

EXAMPLE 55

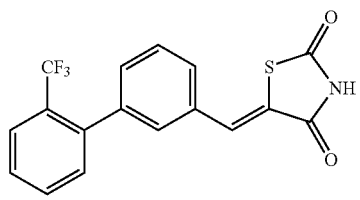

(5Z)-5-{[2'-(trifluoromethyl)-1,1'-biphenyl-3-yl]methylene}-1,3-thiazolidine-2,4-dione Step A: Preparation of 3-formyl-(2'-trifluoromethyl-1,1'-biphenyl To a solution of 3-bromobenzaldehyde (0.37 g, 2 mmol) and (2-trifluoromethyl)phenyl boronic acid (0.42 g, 2.2 mmol) in toluene (20 mL) were added 2M aq. sodium carbonate (2.5 mL) followed by (Ph₃P)₄Pd (0.69 g). The resulting reaction mixture was refluxed for 3 hours, cooled and diluted ethyl acetate. The organic phase was washed with water, saturated aq. sodium bicarbonate, brine and dried over sodium sulfate. The filtrate was concentrated in vacuo and the residue obtained was purified by chromatography (hexane:ethyl acetate; 4:1) to yield the title product as an oil.

¹HNMR (CDCl₃)(δ, ppm): 8.06 (d, 2H), 7.58 (d, 2H), 7.54-7.52 (m, 1H), 7.38-7.35 m, 3H), 2.68 (s, 3H) MS data: m/e 251.2 (M+1)⁺

Step B: 5-(3-(2-trifluoromethyl phenyl)benzylidene)thiazolidine-2,4-dione

To a solution of 3-formyl-(2'-trifluoromethyl-1,1'-biphenyl) (0.334 g, 1.34 mmol) and 2,4-thiazolidinedione (0.19 g, 1.6 mmol) in toluene (20 mL) were added piperidine (0.017 mL, 0.174 mmol) and benzoic acid (0.025 mg, 0.2 mmol), and the reaction was refluxed for 3 h with continuous removal of water. The solvent was then distilled off and the residue was crystallized from ether-pet ether to yield titled product as a solid.

¹H NMR (DMSO-d₆): δ 7.75(s, 1H), 7.61(d, J=8.7 Hz, 2H), 7.28-7.18 (m, 4H), 7.08 (d, J=8.7 Hz, 2H,). MS data: m/e 350 (M+1)⁺

EXAMPLE 56

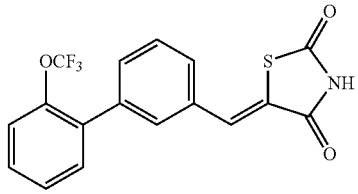

(5Z)-5-{[2'-(trifluoromethoxy)-1,1'-biphenyl-3-yl]methylene}-1,3-thiazolidine-2,4-dione

Step A: Preparation of 3-formyl-(2'-trifluoromethoxy-1,1'-biphenyl)

To a solution of (2-trifluoromethoxy)bromobenzene (0.223 g, 1.5 mmol) and (3-formyl)phenylboronic acid (0.24 g, 1.6 mmol) in n-propanol (3 mL) were added Ph$_3$P (0.036 g, 0.135 mmol), Pd(OAc)2 (0.01 g, 0.045 mmol), 2M aq. sodium carbonate (0.96 mL) and water (0.53mnL). The resulting mixture was refluxed for 4 h, cooled and diluted ethyl acetate. The organic phase was washed with water, saturated aq. sodium bicarbonate, brine and dried over sodium sulfate. The filtrate was concentrated in vacuo and the residue obtained was purified by chromatography (hexane:ethyl acetate; 4:1) to yield the title product as an oil.

$^1$HNMR (CDCl$_3$)(δ, ppm): 8.06 (d, 2H), 7.58 (d, 2H), 7.54-7.52 (m, 1H), 7.38-7.35 m, 3H), 2.68 (s, 3H) MS data: m/e 267.2 (M+1)$^+$

Step B: 5-(3-(2-trifluoromethoxyphenyl)benzylidene)thiazolidine-2,4-dione

To a solution of 3-formyl-(2'-trifluoromethoxy-1,1'-biphenyl) (0.31 g, 1.16 mmol) and 2,4-thiazolidinedione (0.164 g, 1.4 mmol) in toluene (20 mL) were added piperidine (0.015 mL, 0.152 mmol) and benzoic acid (0.021 mg, 0.175 mmol), and the reaction was refluxed for 3 h with continuous removal of water. The solvent was then distilled off and the residue was crystallized from ether-pet ether to yield titled product as a solid.

$^1$H NMR (CDCl$_3$): δ 7.93 (s, 1H), 7.62-7.55 (m, 4H), 7.45-7.28 (m, 4H). MS data: m/e 366.0 (M+1)$^+$

EXAMPLE 57

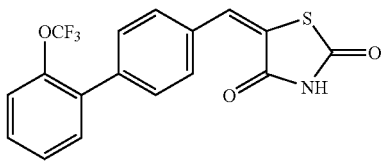

(5E)-5-{[2'-(trifluoromethoxy)-1,1'-biphenyl-4-yl]methylene}-1,3-thiazolidine-2,4-dione

Step A: Preparation of 4-formyl-(2'-trifluoromethoxy-1,1'-biphenyl)

To a solution of (2-trifluoromethoxy)bromobenzene (0.223 g, 1.5 mmol) and (4-formyl)phenylboronic acid (0.24 g, 1.6 mmol) in n-propanol (3 mL) were added Ph$_3$P (0.036 g, 0.135 mmol), Pd(OAc)2 (0.01 g, 0.045 mmol), 2M aq. sodium carbonate (0.96 mL) and water (0.53 mL). The resulting mixture was refluxed for 4 h, cooled and diluted with ethyl acetate. The organic phase was washed with water, saturated aq. sodium bicarbonate, brine and dried over sodium sulfate. The filtrate was concentrated in vacuo and the residue obtained was purified by chromatography (hexane:ethyl acetate; 4:1) to yield the title product as an oil.

$^1$HNMR (CDCl$_3$)(δ, ppm): 8.06 (d, 2H), 7.58 (d, 2H), 7.54-7.52 (m, 1H), 7.38-7.35 m, 3H), 2.68 (s, 3H) MS data: m/e 267.2 (M+1)$^+$

Step B: 5-(4-(2-trifluoromethoxyphenyl)benzylidene)thiazolidine-2,4-dione

To a solution of 4-formyl-(2'-trifluoromethoxy-1,1'-biphenyl) (0.31 g, 1.16 mmol) and 2,4-thiazolidinedione (0.164 g, 1.4 mmol) in toluene (20 mL) were added piperidine (0.015 mL, 0.152 mmol) and benzoic acid (0.021 mg, 0.175 mmol), and the reaction was refluxed for 3 h with continuous removal of water. The solvent was then distilled off and the residue was crystallized from ether-pet ether to yield titled product as a solid.

$^1$H NMR (DMSO-d$_6$): δ 7.75(s, 1H), 7.61(d, J=8.7 Hz, 2H), 7.28-7.18 (m, 4H), 7.08 (d, J=8.7 Hz, 2H,). MS data: m/e 366.9 (N+1)+

EXAMPLE 58

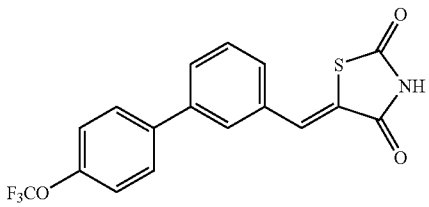

(5Z)-5-{[4'-(trifluoromethoxy)-1,1'-biphenyl-3-yl]methylene}-1,3-thiazolidine-2,4-dione

Step A: Preparation of 3-formyl-(4'-trifluoromethoxy-1,1'-biphenyl)

To a solution of (4-trifluoromethoxy)bromobenzene (0.223 g, 1.5 mmol) and (3-formyl)phenylboronic acid (0.24 g, 1.6 mmol) in n-propanol (3 mL) were added Ph$_3$P (0.036 g, 0.135 mmol), Pd(OAc)2 (0.01 g, 0.045 mmol), 2M aq. sodium carbonate (0.96mnL) and water (0.53 mL). The resulting mixture was refluxed for 4 h, cooled and diluted with ethyl acetate. The organic phase was washed with water, saturated aq. sodium bicarbonate, brine and dried over sodium sulfate. The filtrate was concentrated in vacuo and the residue obtained was purified by chromatography (hexane:ethyl acetate; 4:1) to yield the title product as an oil.

$^1$HNMR (CDCl$_3$)(δ, ppm): 8.06 (d, 2H), 7.58 (d, 2H), 7.54-7.52 (m, 1H), 7.38-7.35 m, 3H), 2.68 (s, 3H) MS data: m/e 267.2 (+1)$^+$

Step B: 5-(3-(4-trifluoromethoxyphenyl)benzylidene)thiazolidine-2,4-dione

To a solution of 3-formyl-(4'-trifluoromethoxy-1,1'-biphenyl) (0.31 g, 1.16 mmol) and 2,4-thiazolidinedione (0.164 g, 1.4 mmol) in toluene (20 mL) were added piperidine (0.015 mL, 0.152 mmol) and benzoic acid (0.021 mg, 0.175 mmol), and the reaction was refluxed for 3 h with continuous removal of water. The solvent was then distilled off and the residue was crystallized from ether-pet ether to yield titled product as a solid.

$^1$HNMR (DMSO-$d_6$): δ 7.75(s, 1H), 7.61(d, J=8.7 Hz, 2H), 7.28-7.18 (m, 4H), 7.08 (d, J=8.7 Hz, 2H,). MS data: m/e 366.9 (M+1)$^+$ Other EXAMPLES of this invention are shown below in TABLE 5:

TABLE 5

| EX. | $R_a$ | $R_c$ | MS Data (m/e, M + 1) |
|---|---|---|---|
| 59 | (4-F)-phenoxy | $(CH_3)_3N^+$—$CH_2$—$CH_2$ | 401.2 |
| 60 | (3,4-methylene-dioxy)-phenoxy | $(CH_3)_3N^+$—$CH_2$—$CH_2$ | 413.2 |
| 61 | (4-Cl)-phenoxy- | H | 332 |
| 62 | (4-Cl)-phenoxy- | $(CH_3)_2N$—$CH_2$—$CH_2$ | 403.9 |
| 63 | Ph | H | 282.3 |
| 64 | (4-F)-phenoxy- | $(i-Pr)_2N$—$CH_2$—$CH_2$ | 358 |
| 65 | (4-F)-phenoxy- | $(CH_2)_4N$—$CH_2$—$CH_2$ | 330.1 |
| 66 | (4-F)-phenoxy- | $(CH_3)_2N$—$CH_2CH(CH_3)$— | 387.1 |
| 67 | (4-F)-phenoxy- | $(CH_3)_2N$—$CH_2CH_2CH_2$— | 401.2 |
| 68 | (4-$CF_3$)-phenoxy- | $(CH_3)_2N$—$CH_2$—$CH_2$ | 437.2 |
| 69 | (4-F)-phenoxy- | N-morpholino-$CH_2$—$CH_2$ | 428.1 |
| 70 | (4-F)-phenoxy- | $NH_2C(O)$—$CH_2$— | 372.2 |
| 71 | (3,4-$CH_3O$)-phenoxy- | HO—$CH_2$—$CH_2$ | 402.1 |
| 72 | (3,4-methylene-dioxy)phenoxy- | H | 342.1 |
| 73 | (3,4-methylene-dioxy)phenoxy- | $(CH_3)_2N$—$CH_2$—$CH_2$ | 413.2 |
| 74 | (4-F)-phenoxy- | $(CH_2)_5N$—$CH_2$—$CH_2$ | 413.3 |
| 75 | Ph | $(CH_3)_2N$—$CH_2$—$CH_2$ | 353.2 |

Other EXAMPLES of this invention are shown below in TABLE 6:

TABLE 6

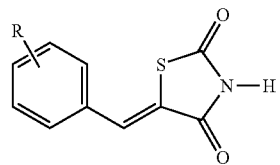

| EX. | R | MS data (m/e, M + 1) |
|---|---|---|
| 76 | 4-(2,6-dichlorophenyl) | 350.1 |
| 77 | 3-(2,6-dichlorophenyl)) | 349.9 |
| 78 | 2-(2,6-dichlorophenyl)) | 350.1 |
| 79 | 3-(2,5-dimethylisoxazolyl) | 303.1 |
| 80 | 4-(2-trfluoromethoxyphenyl-5-bromo) | 443.9 |
| 81 | 3-(2-trifluoromethoxyphenyl-5-bromo) | 444 |
| 82 | 3-(2-thiomethylphenyl) | 328.1 |
| 83 | 3-(2-sulfonylmethylphenyl) | 360 |
| 84 | 3-(2-N,N-diisopropylphenyl) | 381.3 |
| 85 | 3-(2-sulfinylmethylphenyl) | 344.1 |
| 86 | 3-(2-N,N-dimethylphenyl) | 325.1 |
| 87 | 3-(2-cyanophenyl) | 307.2 |
| 88 | 3-(2-isopropylphenyl) | 324.2 |
| 89 | 4-[(2-chloro-4-fluoro)phenyl] | 334 |

TABLE 6-continued

| EX. | R | MS data (m/e, M + 1) |
|---|---|---|
| 90 | 4-(2-fluorophenyl) | 300.1 |
| 91 | 4-(2-t-butoxycarbonylphenyl) | 382.2 |
| 92 | 4-(2-t-butoxycarbonyl aminophenyl) | 397.1 |
| 93 | 4-(2-carboxy-phenyl) | 326 |
| 94 | 4-[(2-CONH—tBu)phenyl} | 380.9 |
| 95 | 3-(2-fluorophenyl) | 300 |
| 96 | 4-[(2-$CONH_2$)phenyl] | 325 |
| 97 | 3-[(2-chloro-4-fluoro)phenyl] | 334.1 |
| 98 | 3-(2-t-butoxycarbonylphenyl) | 382 |
| 99 | 3-(2-$OCH_2CF_3$-phenyl) | 380.2 |
| 100 | 4-(2-$OCH_2CF_3$-phenyl) | 380.1 |
| 101 | 3-(3-isoquinoninyl) | 333 |
| 102 | 4-(3-isoquinoninyl) | 333.1 |
| 103 | 3-(7-benzothienyl) | 338.2 |
| 104 | 3-(2-naphthyl) | 332 |
| 105 | 3-(3-tetrazolyl-phenyl) | 350 |
| 106 | 4-(2-phenoxyphenyl) | 374 |
| 107 | 3-(2-phenoxyphenyl) | 373.9 |
| 108 | 2-(2-phenoxyphenyl) | 374 |
| 109 | 3-(2-benzyloxyphenyl) | 388.2 |
| 110 | 4-(2-benzyloxyphenyl) | 388.1 |
| 111 | 2-(3-$CF_3$-pyrid-2-yl) | 351 |
| 112 | 3-(3-$CF_3$-pyrid-2-yl) | 351 |
| 113 | 4-(3-$CF_3$-pyrid-2-yl) | 351.1 |
| 114 | 3-(2,6-dimethoxyphenyl) | 351 |
| 115 | 3-(2,4-dimethoxyphenyl) | 351 |
| 116 | 3-(2,5-bis-$CF_3$ phenyl) | 417.2 |
| 117 | 4-(2,5-bis-$CF_3$ phenyl) | 417.1 |
| 118 | 3-(4-chloro-2-fluoro phenyl) | 333.2 |
| 119 | 3-(3-$CF_3$ phenyl) | 349 |
| 120 | 3-(2,4-di-fluoro phenyl) | 317.1 |
| 121 | 3-(2,4-di-chloro phenyl) | 350 |
| 122 | 4-(4-chloro-phenyl) | 315 |
| 123 | 4-(2,4-dimethoxyphenyl) | 351.1 |

Other EXAMPLES of this invention are shown below in TABLE 7.

TABLE 7

| EX. | $R_1$ | $R_2$ | MS data m/e, (M + 1) |
|---|---|---|---|
| 124 | 5-(2-fluorophenyl) | 2-Methoxy | 330 |
| 125 | 5-(2,6-dichlorophenyl) | 4-methoxy | 381 |
| 126 | 5-(2-chlorophenyl) | 4-methoxy | 346 |
| 127 | 5-(2-chlorophenyl) | 3,4-dimethoxy | 377 |
| 128 | 4-(2-fluorophenyl) | 2-fluoro | 317.9 |
| 129 | 4-(2-chlorophenyl) | 2-fluoro | 334 |
| 130 | 5-(2-chlorophenyl) | 2-methoxy | 346.2 |
| 131 | 5-(2-fluorophenyl) | 4-methoxy | 330.1 |
| 132 | 5-(2-chlorophenyl) | 3-phenyl | 392.1 |
| 133 | 6-(2-chlorophenyl) | 3-methoxy | 346 |

Other EXAMPLES of this invention are shown below in TABLE 8:

TABLE 8

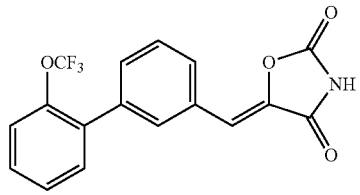

| EX. | R$_1$ | R$_2$ | R | MS Data (m/e, M + 1) |
|---|---|---|---|---|
| 134 | 4-dimethylamino | H | —SO$_2$NHC(CH$_3$)$_3$ | 566 |
| 135 | 4-dimethylamino | H | —SO$_2$NH$_2$ | 510.3 |
| 136 | 4-F | H | —SO$_2$NHC(CH$_3$)$_3$ | 541.1 |
| 137 | 4-F | H | —SO$_2$NH$_2$ | 485 |
| 138 | 4-phenyl | H | —SO$_2$NHC(CH$_3$)$_3$ | 599.2 |
| 139 | 4-phenyl | H | —SO$_2$NH$_2$ | 543.2 |
| 140 | 2-Cl | 3-Cl | —SO$_2$NHC(CH$_3$)$_3$ | 591 |
| 141 | 2-Cl | 3-Cl | —SO$_2$NH$_2$ | 535 |
| 142 | 4-(4-F)phenoxy | H | —SO$_2$NHC(CH$_3$)$_3$ | 633.2 |
| 143 | 4-(4-F)phenoxy | H | —SO$_2$NH$_2$ | 577.3 |
| 144 | 3-(4-Cl)phenoxy | H | —SO$_2$NHC(CH$_3$)$_3$ | 649 |
| 145 | 3-(4-Cl)phenoxy | H | —SO$_2$NH$_2$ | 593 |
| 146 | 4-CH$_3$O | H | —SO$_2$NHC(CH$_3$)$_3$ | 553 |
| 147 | 4-CH$_3$O | H | —SO$_2$NH$_2$ | 497.1 |
| 148 | 4-(3,4-methylenedioxy)phenoxy | H | —SO$_2$NHC(CH$_3$)$_3$ | 659 |
| 149 | 4-(3,4-methylenedioxy)phenoxy | H | —SO$_2$NH$_2$ | 603.2 |

EXAMPLE 150

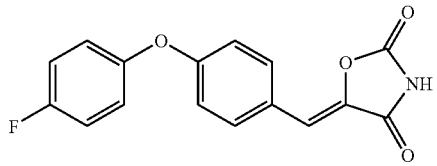

(5Z)-5-[4-(4-fluorophenoxy)benzylidene]-1,3-oxazolidine-2,4-dione

The title compound was prepared by reacting 4-(4-fluorophenoxy)benzaldehyde (from Step A in Example 1) with oxazolidine-2,5-dione in toluene in the presence of piperidine and acetic acid with continuous removal of water, as described in Step B of Example 1. The crystalline product collected was washed with petroleum ether on the filter and dried in vacuo.

$^1$H NMR (DMSO-d$_6$): δ 7.70 (s, 1H), 7.61(d, J=8.7 Hz, 2H), 7.28-7.18 (m, 4H), 7.08 (d, J=8.7 Hz, 2H,). MS (ESI): m/e 299.9 (M+1)$^+$

EXAMPLE 151

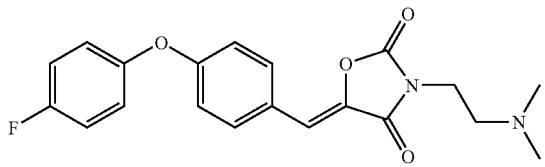

(5Z)-3-[2-(dimethylamino)ethyl]-5-[4-(4-fluorophenoxy)benzylidene]-1,3-oxazolidine-2,4-dione The title compound was prepared by reacting 5-(4-(4-fluorophenoxy)benzylidene)oxazolidine-2,5-dione (from Example 145) with chloro-N,N-dimethylaminoethane in a 1:1 mixture of THF and DMF in the presence of added anhydrous K$_2$CO$_3$ as described in Example 5.

$^1$HNMR (CD$_3$)$_2$CO): δ 7.78 (s, 1H), 7.66 (d, J=8.7 Hz, 2H), 7.26-7.12 (m, 4H), 7.10 (d, J=8.7 Hz, 2H,), 3.84 (t, J$_1$=12.8 Hz, J$_2$=6 Hz, 2H), 2.56 (t, J$_3$=12.8 Hz, J$_2$=6 Hz, 2H), 2.22 (s, 6H). MS (ESI): m/e 371.1 (M+1)$^+$

EXAMPLE 152

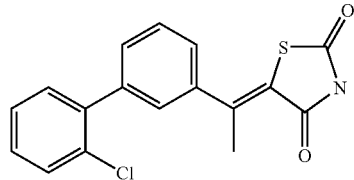

(5Z)-5-{[2'-(trifluoromethoxy)-1,1'-biphenyl-3-yl]methylene}-1,3-oxazolidine-2,4-dione The title compound was prepared by reacting 3-formyl-(2'-trifluoromethoxy-1,1'-biphenyl) (from Example 56, Step A) with 2,4-oxazolidinedione in toluene in the presence of piperidine and benzoic acid as described in Example 56, Step B.

$^1$H NMR (CDCl$_3$): δ 7.86 (s, 1H), 7.62-7.55 (m, 4H), 7.45-7.28 (m, 4H). MS data: m/e 350.1(+1)$^+$

EXAMPLE 153

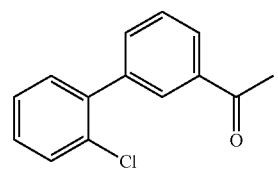

(5Z)-5-[1-(2'-chloro-1,1'-biphenyl-3-yl)ethylidene]-1,3-thiazolidine-2,4-dione

Step A: 1-(2'-chloro-1,1'-biphenyl-3-yl)ethanone

To a solution of iodochlorobenzene (8.64 g, 55 mmol) in n-propanol (85.8 mL), 3-acetylphenylboronic acid (10.0 g, 50 mmol) was added and the solution was stirred for 2 min. Then triphenylphosphine (118 mg, 0.45 mmol), palladium acetate (33 mg, 0.15 mmol), 2M sodium carbonate (30 mL, 60 mmol) and water (17.68 mL) were added and the reaction mixture was refluxed for 16 h. It was quenched with water and partitioned between ethyl acetate and water, washed with saturated sodium bicarbonate, brine and dried over sodium sulfate. Finally it was filtered, concentrated and purified by chromatography (hexane:ethyl acetate; 4:1) to yield the product.

$^1$HNMR (CDCl$_3$)($\delta$, ppm): 8.06 (d, 2H), 7.58 (d, 2H), 7.54-7.52 (m, 1H), 7.38-7.35 (m, 3H), 2.68 (s, 3H). MS data: m/e 231.1 (M+1).

Step B: (5Z)-5-[1-(2'-chloro-1,1'-biphenyl-3-yl)ethylidene]-1,3-thiazolidine-2,4-dione To a solution of 1-(2'-chloro-1,1'-biphenyl-3-yl)ethanone (145 mg, 0.63 mmol) and 2,4-thiazolidinedione (67 mg, 0.57 mmol) in xylene (1.9 mL), sodium acetate (38 mg, 0.28 mmol) and acetic anhydride (53 µL, 0.57 mmol) were added and the solution was heated in a sealed tube for 16 h. It was then cooled to rt, partitioned between ethyl acetate and water, washed with saturated sodium bicarbonate, brine and dried over sodium sulfate. Finally filtered, concentrated and purified by chromatography. (hexanes:ethyl acetate; 4:1) to give the product as a solid.

HNMR (CDCl$_3$)($\delta$, ppm): 8.55 (s, 1H), 7.55-7.51 (m, 3H), 7.45 (s, 1H), 7.39-7.34 (m, 4H), 2.80 (m, 3H). MS data: m/e 329.9 (M+1).

EXAMPLE 154

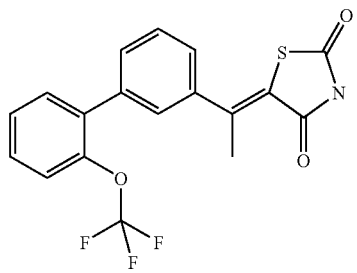

(5Z)-5-[1-(2'-trifluoromethoxy-1,1'-biphenyl-3-yl) ethylidene]-1,3-thiazolidine-2,4-dione.

Step A: 1-(2'-trifluoromethoxy-1,1'-biphenyl-3-yl) ethanone

The 1-(2'-trifluoromethoxy-1,1'-biphenyl-3-yl)ethanone was prepared by the procedure described for Example 153 (Step A).

HNMR (CDCl$_3$)($\delta$, ppm): 8.09 (s, 1H), 8.06 (d, 1H), 7.71 (d,2H), 7.58 (t, 1H), 7.50-7.40(m, 4H), 2.67 (s, 3H). MS data: m/e 281.1 (M+1).

Step B: (5Z)-5-[1-(2'-trifluoromethoxy-1,1'-biphenyl-3-yl)ethylidene]-1,3-thiazolidine-2,4-dione The titled compound was prepared by the procedure described for Example 153 (Step B).

$^1$HNMR (CDCl$_3$)($\delta$, ppm): 8.40 (s, 1H), 7.56-7.51 (m, 2H), 7.47-7.36 (m, 6H), 2.790 (m, 3H). MS data: m/e 380.1 (M+1).

Other variations or modifications, which will be obvious to those skilled in the art, are within the scope and teachings of this invention. This invention is not to be limited except as set forth in the following claims.

What is claimed is:

1. A method of treating pain in a patient in need thereof comprising administering to said patient an effective amount of a compound represented by Formula (IA) or (IB):

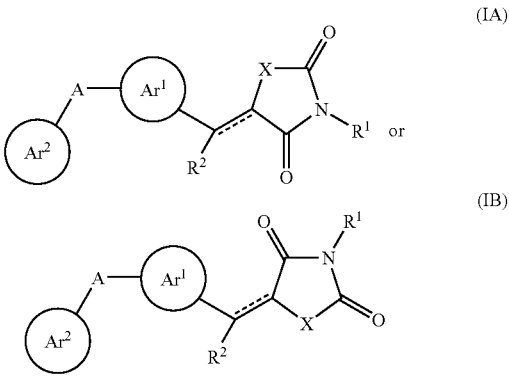

or a pharmaceutically acceptable salt thereof, wherein
X is —S—;
R$^1$ is hydrogen, —C$_{1-4}$alkyl, —C$_{1-4}$alkyl-N(C$_{0-4}$alkyl) (C$_{0-4}$alkyl), —C$_{0-4}$alkyl-CO—N(C$_{0-4}$alkyl)(C$_{0-4}$alkyl), —C$_{0-4}$alkyl-CO—O(C$_{0-4}$alkyl), —C$_{1-4}$alkyl-piperidinyl, —C$_{1-4}$alkyl-morpholinyl, —C$_{1-4}$alkyl-pyrrolidinyl, —C$_{1-4}$alkyl-aryl, —C$_{1-4}$alkyl-aryl-aryl, optionally substituted with 1-6 independent halogen, —CN, —NO$_2$, —C$_{1-4}$alkyl, —O—C$_{1-4}$alkyl, —N(C$_{0-4}$alkyl) (C$_{0-4}$alkyl), —C$_{0-4}$alkyl-CO—O(C$_{0-4}$alkyl), —(C$_{0-4}$ alkyl)-NH—CO—O(C$_{0-4}$alkyl), —(C$_{0-4}$alkyl)-CO—N (C$_{0-4}$alkyl)(C$_{0-4}$alkyl), —S(C$_{0-4}$alkyl), —S(O)(C$_{1-4}$ alkyl), —SO$_2$(C$_{1-4}$alkyl), —SO$_2$N(C$_{0-4}$alkyl)(C$_{0-4}$ alkyl), or —NHSO$_2$(C$_{1-4}$alkyl) substituents;
R$^2$ is —C$_{0-4}$alkyl;
Ar$^1$ is phenyl, optionally substituted with 1-4 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N (C$_{0-4}$alkyl)(C$_{0-4}$alkyl), x) —S(C$_{0-4}$alkyl), xi) —S(O) (C$_{1-4}$alkyl), xii) —SO$_2$(C$_{1-4}$alkyl), xiii) —SO$_2$N (C$_{0-4}$ alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N (C$_{0-6}$alkyl)(C$_{0-6}$alkyl), xvi) —C$_{1-10}$alkyl in which one or more of the alkyl carbons is replaced by a —N(C$_{0-6}$ alkyl)-, —O—, —S(O)$_{1,2}$—, —O—O(O)—, —C(O)——C(O)—N(C$_{0-6}$alkyl)-, —N(C$_{0-6}$alkyl)-C (O)—, —N(C$_{0-6}$alkyl)-C(O)—N(C$_{0-6}$alkyl-, —C(O)—, —CH(OH)—, —C=C—, —C≡C—, optionally substituted with 1-6 independent —CHO aryl, aryloxy-, —N(C$_{0-6}$alkyl)(C$_{0-6}$alkyl), —N(C$_{0-6}$ alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—

N(C$_{0-6}$alkyl)(C$_{0-6}$alkyl), —O—C(O)—N(C$_{0-6}$alkyl)(C$_{0-6}$alkyl), —C(O)—N($_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents;

Ar$^2$ is phenyl, optionally substituted with 1-5 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{0-6}$alkyl)(C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N($_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix —C$_{0-4}$alkyl-O—C(O)—C$_{0-4}$alkyl substituents, provided that when R$^1$ is hydrogen the substituents of Ar$^2$ cannot be halogen, —CN, —NO$_2$, —O—C$_{1-4}$alkyl, —NHSO$_2$(C$_{1-4}$alkyl), or —SO$_2$(C$_{1-4}$alkyl);

A is —O—, —S—, —CH$_2$—, —N(C$_{0-4}$alkyl)-, or absent;

wherein aryl is phenyl, optionally substituted with 1-6 independent i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{1-4}$alkyl), xiii) —SO$_2$N(C$_{0-4}$alkyl)(C$_{0-4}$alkyl), xiv) —NHSO$_2$(C$_{1-4}$alkyl), xv) —C$_{1-10}$alkyl optionally substituted with 1-6 independent —CHO, —O—C$_{1-4}$alkyl, aryl, aryloxy-, —N(C$_{1-6}$alkyl)(C$_{0-6}$alkyl), —N(C$_{0-6}$alkyl)-C(O)—C$_{0-6}$alkyl), —OPO(OH)O-M$^+$, —OSO$_3$-M$^+$, —O—CO(C$_{1-3}$alkyl)CO$_2$-M$^+$, —O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvi) —C$_{1-10}$alkyl in which one or more of the alkyl carbons is replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, —C≡C—, optionally substituted with 1-6 independent —CHO, aryl, aryloxy-, —N(C$_{0-6}$alkyl)(C$_{0-6}$alkyl), —N(C$_{0-6}$alkyl)-C(O)—(C$_{0-6}$alkyl), —OPO(OH)O-M$^+$, —OSO$_3$-M$^+$, —O—CO(C$_{1-3}$alkyl)CO$_2$-M$^+$, O—CO—(C$_{1-6}$alkyl)-N(C$_{0-6}$alkyl)(C$_{0-6}$alkyl), —O—C(O)—C$_{0-6}$alkyl, —N(C$_{0-6}$alkyl)-C(O)—N(C$_{0-6}$alkyl)(C$_{0-6}$alkyl), —O—C(O)—N(C$_{0-6}$alkyl)(C$_{0-6}$alkyl), —C(O)—N(C$_{0-6}$alkyl)(C$_{0-6}$alkyl), xvii) —S(O)$_{1-2}$—(C$_{1-6}$alkyl)-, xviii) —C$_{0-4}$alkyl-C$_{3-6}$cycloalkyl, or xix) —C$_{0-4}$alkyl-O—C(O)—C$_{0-4}$alkyl substituents;

M$^+$ is ammonium, sodium, lithium, potassium, calcium, magnesium, dicyclohexylamine, N-methyl-D-glucanine, arginine, or lysine; and any alkyl is optionally substituted with 1-6 independent halogen, phenyl, naphthyl, —N(C$_{0-4}$alkyl)(C$_{0-4}$alkyl), —C(O)—O(C$_{0-4}$alkyl), —CN, —NH—C(O)—O(C$_{0-4}$alkyl), —S(C$_{0-4}$alkyl), —NHSO$_2$(C$_{0-4}$alkyl)(C$_{0-4}$alkyl), or —SO$_2$N(C$_{0-4}$alkyl)(C$_{0-4}$alkyl) substituent.

2. The method according to claim 1 wherein said compound is represented by Formula (IA), or a pharmaceutically acceptable salt thereof.

3. The method according to claim 1 wherein said compound is represented by Formula (IB), or a pharmaceutically acceptable salt thereof.

4. A compound represented by

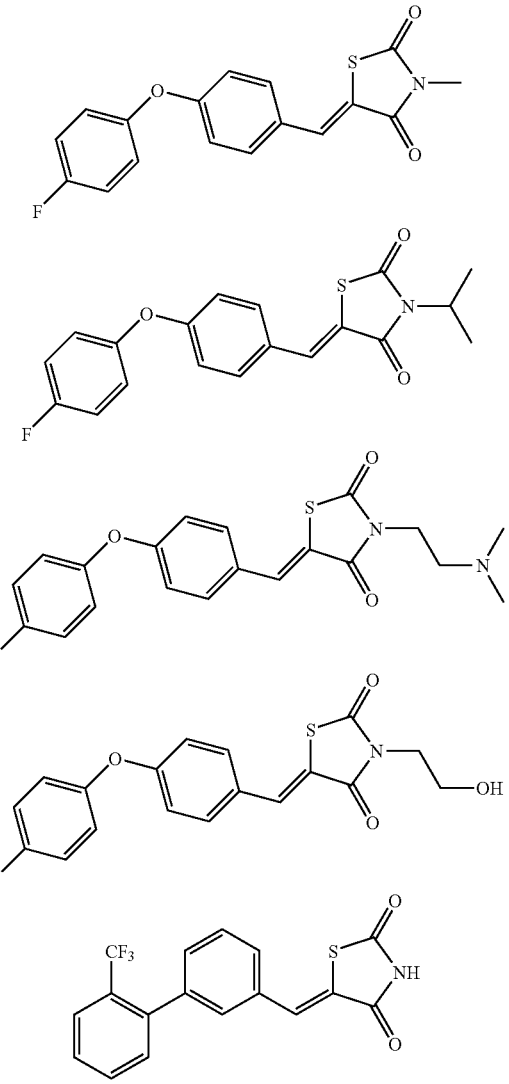

-continued

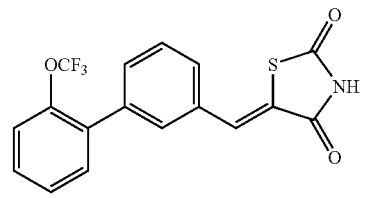

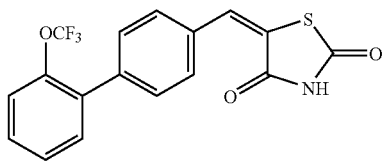

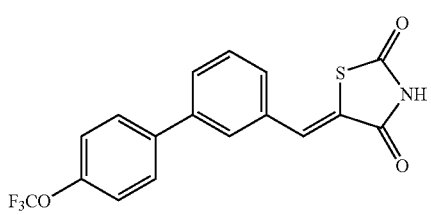

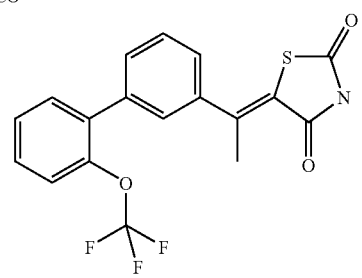

or a pharmaceutically acceptable salt thereof.

5. A compound represented by

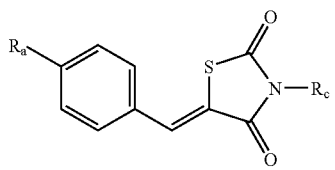

| Ra | Rc |
|---|---|
| (4-F)-phenoxy | $(CH_3)_3N^+-CH_2-CH_2$ |
| (3,4-methylene-dioxy)-phenoxy | $(CH_3)_3N^+-CH_2-CH_2$ |
| (4-Cl)-phenoxy- | $(CH_3)_2N-CH_2-CH_2$ |
| (4-F)-phenoxy- | $(i-Pr)_2N-CH_2-CH_2$ |
| (4-F)-phenoxy- | $(CH_2)_4N-CH_2-CH_2$ |
| (4-F)-phenoxy- | $(CH_3)_2N-CH_2CH(CH_3)-$ |
| (4-F)-phenoxy- | $(CH_3)_2N-CH_2CH_2CH_2-$ |
| (4-CF$_3$)-phenoxy- | $(CH_3)_2N-CH_2-CH_2$ |
| (4-F)-phenoxy- | N-morpholino-$CH_2-CH_2$ |
| (4-F)-phenoxy- | $NH_2C(O)-CH_2-$ |
| (3,4-CH$_3$O)-phenoxy- | $HO-CH_2-CH_2$ |
| (3,4-methylenedioxy)phenoxy- | H |
| (3,4-methylenedioxy)phenoxy- | $(CH_3)_2N-CH_2-CH_2$ |
| (4-F)-phenoxy- | $(CH_2)_5N-CH_2-CH_2$ |
| Ph | $(CH_3)_2N-CH_2-CH_2$ | or a pharmaceutically acceptable salt thereof.

6. A compound represented by

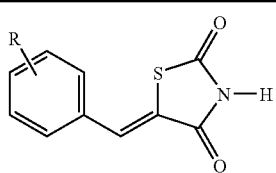

| R |
|---|
| 4-(2-trfluoromethoxyphenyl-5-bromo) |
| 3-(2-trifluoromethoxyphenyl-5-bromo) |
| 3-(2-thiomethylphenyl) |
| 3-(2-N,N-diisopropylphenyl) |
| 3-(2-sulfinylmethylphenyl) |
| 3-(2-N,N-dimethylphenyl) |
| 3-(2-isopropylphenyl) |
| 4-(2-t-butoxycarbonylphenyl |
| 4-(2-t-butoxycarbonyl aminophenyl |
| 4-(2-carboxy-phenyl) |
| 3-(2-t-butoxycarbonylphenyl) |
| 3-(2-OCH$_2$CF$_3$-phenyl) |
| 4-(2-OCH$_2$CF$_3$-phenyl) |
| 4-(2-phenoxyphenyl) |
| 3-(2-phenoxyphenyl) |
| 2-(2-phenoxyphenyl) |
| 3-(2-benzyloxyphenyl) |
| 4-(2-benzyloxyphenyl) |
| 3-(2,5-bis-CF$_3$ phenyl) |
| 4-(2,5-bis-CF$_3$ phenyl) |
| 3-(3-CF$_3$ phenyl) | or a pharmaceutically acceptable salt thereof.

7. A compound represented by

| R$_1$ | R$_2$ | R |
|---|---|---|
| 4-dimethylamino | H | $-SO_2NHC(CH_3)_3$ |
| 4-dimethylamino | H | $-SO_2NH_2$ |
| 4-F | H | $-SO_2NHC(CH_3)_3$ |
| 4-F | H | $-SO_2NH_2$ |
| 4-phenyl | H | $-SO_2NHC(CH_3)_3$ |
| 4-phenyl | H | $-SO_2NH_2$ |
| 2-Cl | 3-Cl | $-SO_2NHC(CH_3)_3$ |
| 2-Cl | 3-Cl | $-SO_2NH_2$ |
| 4-(4-F)phenoxy | H | $-SO_2NHC(CH_3)_3$ |
| 4-(4-F)phenoxy | H | $-SO_2NH_2$ |
| 3-(4-Cl)phenoxy | H | $-SO_2NHC(CH_3)_3$ |
| 3-(4-Cl)phenoxy | H | $-SO_2NH_2$ |
| 4-CH$_3$O | H | $-SO_2NHC(CH_3)_3$ |
| 4-CH$_3$O | H | $-SO_2NH_2$ |
| 4-(3,4-methylene-dioxy)phenoxy | H | $-SO_2NHC(CH_3)_3$ |
| 4-(3,4-methylene-dioxy)phenoxy | H | $-SO_2NH_2$ | or a pharmaceutically acceptable salt thereof.

8. A pharmaceutical composition comprising: a therapeutically effective amount of the compound according to claim 4, or a pharmaceutically acceptable salt thereof; and a pharmaceutically acceptable carrier.

9. A method of treatment of pain comprising the step of administering a therapeutically effective amount of the compound according to Formula (IA) or (IB), or a pharmaceutically acceptable salt thereof, as defined in claim 1.

10. A method of treatment of chronic, visceral, inflammatory and neuropathic pain comprising the step of administering a therapeutically effective amount of the compound according to Formula (IA) or (IB), or a pharmaceutically acceptable salt thereof, as defined in claim 1.

11. A method of treatment of pain resulting from traumatic nerve injury, nerve compression or entrapment, postherpetic neuralgia, trigeniinal neuralgia, diabetic neuropathy, chronic lower back pain, phantom limb pain, and pain resulting from cancer and chemotherapy comprising the step of administering a therapeutically effective amount of the compound according to Formula (IA) or (IB), or a pharmaceutically acceptable salt thereof, as defined in claim 1.

12. A pharmaceutical composition comprising: a compound according to claim 5, or a pharmaceutically acceptable salt thereof; and a pharmaceutically acceptable carrier.

* * * * *